United States Patent
Green et al.

(10) Patent No.: US 12,078,643 B2
(45) Date of Patent: *Sep. 3, 2024

(54) ALPHA-SYNUCLEIN DETECTION ASSAY AND METHOD FOR DIAGNOSING ALPHA-SYNUCLEINOPATHIES

(71) Applicant: The University Court of the University of Edinburgh, Midlothian (GB)

(72) Inventors: Alison Green, Midlothian (GB); Graham Fairfoul, Midlothian (GB)

(73) Assignee: The University Court of the University of Edinburgh, Edinburgh (GB)

( * ) Notice: Subject to any disclaimer, the term of this patent is extended or adjusted under 35 U.S.C. 154(b) by 588 days.

This patent is subject to a terminal disclaimer.

(21) Appl. No.: 17/314,531

(22) Filed: May 17, 2021

(65) Prior Publication Data

US 2021/0263049 A1    Aug. 26, 2021

Related U.S. Application Data

(63) Continuation of application No. 16/315,854, filed as application No. PCT/GB2017/051988 on Jul. 6, 2017, now Pat. No. 11,099,197.

(30) Foreign Application Priority Data

Jul. 7, 2016    (GB) ..................... 1611840

(51) Int. Cl.
*G01N 33/68*    (2006.01)
*G01N 21/64*    (2006.01)
*G01N 33/58*    (2006.01)

(52) U.S. Cl.
CPC ..... *G01N 33/6896* (2013.01); *G01N 21/6428* (2013.01); *G01N 33/582* (2013.01); *G01N 2021/6439* (2013.01); *G01N 2333/4709* (2013.01); *G01N 2800/2814* (2013.01); *G01N 2800/2835* (2013.01); *G01N 2800/7047* (2013.01)

(58) Field of Classification Search
CPC ....... G01N 33/6896; G01N 2333/4709; G01N 2800/2835; G01N 2800/7047; G01N 33/582; G01N 21/6428; G01N 2021/6439
See application file for complete search history.

(56) References Cited

U.S. PATENT DOCUMENTS

| 2011/0293520 A1 | 12/2011 | Giese et al. |
| 2016/0077111 A1 | 3/2016 | Jara et al. |
| 2016/0077112 A1 | 3/2016 | Jara et al. |

FOREIGN PATENT DOCUMENTS

| JP | 2016514266 A | 5/2016 |
| WO | 2004073651 A2 | 9/2004 |
| WO | 2014138919 A1 | 9/2014 |
| WO | 2016040907 A1 | 3/2016 |
| WO | 20216040907 A1 | 3/2016 |

OTHER PUBLICATIONS

International Search Report and Written Opinion mailed Sep. 18, 2017, for Application No. PCT/GB2017/051988 filed Jul. 6, 2017 (15 pages).
Atarashi et al. Ultrasensitive human prion detection in cerebrospinal fluid by real-time quaking-induced conversion. Nat Med. Feb. 2011;17(2):175-8. doi: 10.1038/nm.2294. Epub Jan. 30, 2011.
Bernis et al. Prion-like propagation of human brain-derived alpha-synuclein in transgenic mice expressing human wild-type alpha-synuclein. Acta Neuropathol Commun. Nov. 26, 2015;3:75.
Brandel et al. La maladie de Parkinson est-elle une maladie è prion? [Is Parkinson's disease a prion disease?]. Rev Neurol (Paris). Dec. 2015;171(12):812-24. French. doi: 10.1016/j.neurol.2015.10.005. Epub Nov. 10, 2015.
Clarke et al. Folate, vitamin B12, and serum total homocysteine levels in confirmed Alzheimer disease. Arch Neurol. Nov. 1998;55(11):1449-55.
Denkers et al. Enhanced prion detection in biological samples by magnetic particle extraction and real-time quaking-induced conversion. J Gen Virol. Aug. 2016;97(8):2023-2029. doi: 10.1099/jgv.0.000515. Epub May 27, 2016.
Fairfoul et al. Alpha-synuclein RT-QuIC in the CSF of patients with alpha-synucleinopathies. Ann Clin Transl Neurol. Aug. 28, 2016;3(10):812-818.
Giehm et al. Strategies to increase the reproducibility of protein fibrillization in plate reader assays. Anal Biochem. May 15, 2010;400(2):270-81. doi: 10.1016/j.ab.2010.02.001. Epub Feb. 10, 2010. Erratum in: Anal Biochem. Nov. 15, 2010;406(2):e1.
Giehm et al. Assays for α-synuclein aggregation. Methods. Mar. 2011;53(3):295-305. doi: 10.1016/j.ymeth.2010.12.008. Epub Dec. 14, 2010.
Goedert et al. 100 years of Lewy pathology. Nat Rev Neurol. Jan. 2013;9(1):13-24. doi: 10.1038/nrneurol.2012.242. Epub Nov. 27, 2012.

(Continued)

*Primary Examiner* — Kimberly Ballard
(74) *Attorney, Agent, or Firm* — ArentFox Schiff LLP; Shawn P. Foley

(57) ABSTRACT

A method of detecting the presence of alpha-synuclein aggregation in a biological sample is provided whereby a biological sample is mixed with a reaction sample comprising a population of beads, a fluorophore adapted to bind to protein aggregates and to increase fluorescence when bound to protein aggregates, and alpha-synuclein or a fragment or variant thereof to form a reaction mixture, the reaction mixture is illuminated and at the same time incubated with intermittent agitation cycles, wherein a significant increase in the fluorescence of the reaction mixture during incubation is indicative of the presence of aggregates of alpha-synuclein in the biological sample. Method of diagnosing alpha-synucleinopathies such as Parkinson's disease or Dementia with Lewy Bodies.

16 Claims, 19 Drawing Sheets

Specification includes a Sequence Listing.

(56) References Cited

OTHER PUBLICATIONS

Goya et al. Probiotic Bacillus subtilis Protects against α-Synuclein Aggregation in C. elegans. Cell Rep. Jan. 14, 2020;30(2):367-380. e7.
Groveman et al. Correction to: Rapid and ultra-sensitive quantitation of disease-associated α-synuclein seeds in brain and cerebrospinal fluid by αSyn RT-QuIC. Acta Neuropathol Commun. Nov. 5, 2020;8(1):180. doi: 10.1186/s40478-020-01052-y. Erratum for. Acta Neuropathol Commun. Feb. 9, 2018;6(1):7.
Haley et al. Prion-seeding activity in cerebrospinal fluid of deer with chronic wasting disease. PLoS One. Nov. 25, 2013;8(11):e81488.
Hierva et al. Anti-amyloid compounds inhibit α-synuclein aggregation induced by protein misfolding cyclic amplification (PMCA). J Biol Chem. Apr. 25, 2014;289(17):11897-11905. doi: 10.1074/jbc.M113.542340. Epub Feb. 28, 2014.
Hong et al. DJ-1 and alpha-synuclein in human cerebrospinal fluid as biomarkers of Parkinson's disease. Brain. Mar. 2010;133(Pt 3):713-26. doi: 10.1093/brain/awq008. Epub Feb. 15, 2010.
Hughes et al. Accuracy of clinical diagnosis of idiopathic Parkinson's disease: a clinico-pathological study of 100 cases. J Neurol Neurosurg Psychiatry. Mar. 1992;55(3):181-4.
Iranzo et al. Neurodegenerative disease status and post-mortem pathology in idiopathic rapid-eye-movement sleep behaviour disorder: an observational cohort study. Lancet Neurol. May 2013;12(5):443-53. doi: 10.1016/S1474-4422(13)70056-5. Epub Apr. 3, 2013.
Kovacs et al. Mixed brain pathologies in dementia: the BrainNet Europe consortium experience. Dement Geriatr Cogn Disord. 2008;26(4):343-50. doi: 10.1159/000161560. Epub Oct. 10, 2008.
Kruse et al. Validation of a quantitative cerebrospinal fluid alpha-synuclein assay in a European-wide interlaboratory study. Neurobiol Aging. Sep. 2015;36(9):2587-96. doi: 10.1016/j.neurobiolaging. 2015.05.003. Epub May 15, 2015.
Martí et al. Clinical overview of the synucleinopathies. Mov Disord. Sep. 2003;18 Suppl 6:S21-7.
McGuire et al. Real time quaking-induced conversion analysis of cerebrospinal fluid in sporadic Creutzfeldt-Jakob disease. Ann Neurol. Aug. 2012;72(2):278-85.
Mollenhauer et al. Direct quantification of CSF alpha-synuclein by ELISA and first cross-sectional study in patients with neurodegeneration. Exp Neurol. Oct. 2008;213(2):315-25. doi: 10.1016/j.expneurol. 2008.06.004. Epub Jun. 14, 2008.
Montine et al. National Institute on Aging; Alzheimer's Association. National Institute on Aging-Alzheimer's Association guidelines for the neuropathologic assessment of Alzheimer's disease: a practical approach. Acta Neuropathol. Jan. 2012;123(1):1-11. doi: 10.1007/s00401-011-0910-3. Epub Nov. 20, 2011.
Neurauter et al. Cell isolation and expansion using Dynabeads. Adv Biochem Eng Biotechnol. 2007;106:41-73.
Ohrfelt et al. Cerebrospinal fluid alpha-synuclein in neurodegenerative disorders—a marker of synapse loss? Neurosci Lett. Feb. 6, 2009;450(3):332-5. doi: 10.1016/j.neulet.2008.11.015. Epub Nov. 12, 2008.
Orrú et al. Prion disease blood test using immunoprecipitation and improved quaking-induced conversion. mBio. May 10, 2011;2(3):e00078-11.
Park et al. Establishment of Method for the Determination of Aggregated α-Synuclein in DLB Patient Using RT-QuIC Assay. Protein Pept Lett. 2021;28(1):115-120.
Pérez-Pi et al. α-Synuclein-Confocal Nanoscanning (ASYN-CONA), a Bead-Based Assay for Detecting Early-Stage α-Synuclein Aggregation. Anal Chem. May 7, 2019;91(9):5582-5590. doi: 10.1021/acs.analchem.8b03842. Epub Apr. 18, 2019.
Quy et al. Synthesis of Silica-Coated Magnetic Nanoparticles and Application in the Detection of Pathogenic Viruses. J Nanomater vol. 2013, Article ID 603940, 6 pages, 2013.
Rolinski et al. Visual short-term memory deficits in REM sleep behaviour disorder mirror those in Parkinson's disease. Brain. Jan. 2016;139(Pt 1):47-53. doi: 10.1093/brain/awv334. Epub Nov. 18, 2015.
Ruffman et al. Gut Feelings About α-Synuclein in Gastrointestinal Biopsies: Biomarker in the Making? Mov Disord. Feb. 2016;31(2):193-202. doi: 10.1002/mds.26480. Epub Jan. 22, 2016.
Shi et al. Cerebrospinal fluid biomarkers for Parkinson disease diagnosis and progression. Ann Neurol. Mar. 2011;69(3):570-80. doi: 10.1002/ana.22311. Epub Mar. 11, 2011.
Spillantini et al. Assignment of human alpha-synuclein (SNCA) and beta-synuclein (SNCB) genes to chromosomes 4q21 and 5q35. Genomics. May 20, 1995;27(2):379-81.
Szewczyk-Krolikowski et al. The influence of age and gender on motor and non-motor features of early Parkinson's disease: initial findings from the Oxford Parkinson Disease Center (OPDC) discovery cohort. Parkinsonism Relat Disord. Jan. 2014;20(1):99-105. doi: 10.1016/j.parkreldis.2013.09.025. Epub Oct. 12, 2013.
Wikipedia, "Dynabeads," accessed from wikipedia.org on Jun. 4, 2020 (Year:2020).
Williams et al. Oligomeric α-synuclein and β-amyloid variants as potential biomarkers for Parkinson's and Alzheimer's diseases. Eur J Neurosci. Jan. 2016;43(1):3-16. doi: 10.1111/ejn. 13056. Epub Oct. 15, 2015.
International Preliminary Report on Patentability related to International Application No. PCT/GB2017/051988 dated Jan. 8, 2019.
Canadian Intellectual Property Office, Examination Search Report issued in Canadian Application No. 3029204 dated Mar. 28, 2023 (4 pages).
IP Australia, Examination Report No. 1 issued in Australian Application No. 2017292377 dated Aug. 26, 2022 (5 pages).
European Patent Office, Examination Report issued in European Application No. 17742509.7 dated Apr. 11, 2023 (4 bages).
European Patent Office, Examination Report issued in European Application No. 17742509.7 dated Sep. 29, 2021 (5 pages).
The Patent Office of the P.R.C., First Office Action issued in Chinese Application No. 201780041987.3 dated Aug. 26, 2021 (8 pages).
Atarashi, R. et al., "Real-time quaking-induced conversion: a highly sensitive assay for prion detection," Prion, vol. 5, No. 3, Jun. 28, 2011, pp. 150-153 (4 pages).
The Patent Office of the P.R.C., Second Office Action issued in Chinese Application No. 201780041987.3 dated Jan. 29, 2022 (7 pages).
The Patent Office of the P.R.C., Third Office Action issued in Chinese Application No. 201780041987.3 dated Apr. 14, 2022 (6 pages).
The Patent Office of the P.R.C., Fourth Office Action issued in Chinese Application No. 201780041987.3 dated Dec. 1, 2022 (9 pages).
IP Australia, Examination Report No. 2 issued in Australian Application No. 2017292377 dated Dec. 5, 2022 (3 pages).
Korean Intellectual Property Office, Notice to Submit Response issued in Korean Application No. 10-2019-7003376 dated Mar. 19, 2021 (4 pages).
Japanese Patent Office, Notice of Reasons for Rejection issued in Japanese Application No. 2019-500334 dated Mar. 29, 2021 (8 pages).

A

B

A

B

A

B

ALPHA-SYNUCLEIN DETECTION ASSAY AND METHOD FOR DIAGNOSING ALPHA-SYNUCLEINOPATHIES

CROSS-REFERENCE TO RELATED APPLICATIONS

This application is a continuation of U.S. application Ser. No. 16/315,854 filed on Jan. 7, 2019, which is a U.S. national stage application under 35 U.S.C. § 371 of International Application No. PCT/GB2017/051988 filed on Jul. 6, 2017, which in turn claims priority to Great Britain Application No. 1611840.8 filed Jul. 7, 2016, the contents of which are incorporated by reference herein in their entireties for all purposes.

INCORPORATION BY REFERENCE OF SEQUENCE LISTING

The instant application contains a Sequence Listing which has been submitted electronically in ASCII format and is hereby incorporated by reference in its entirety. Said ASCII copy, created on May 6, 2022 and is 2 KB in size, is named HGF-106CON_ST25.txt.

FIELD OF THE INVENTION

The invention relates to an assay for the detection of aggregated proteins in a biological sample, more specifically to an assay for the detection of aggregated alpha-synuclein in a biological sample.

BACKGROUND OF THE INVENTION

Alpha-synuclein (a-syn) is a well conserved, small acidic protein of 140-amino acids and a molecular weight of 19 kDa that is encoded by the SNCA gene located on chromosome 4.1 It is located in high concentration in the presynaptic nerve terminals within the central nervous system where it plays a role in synaptic vesicle biology.[2] The synucleinopathies are a set of neurodegenerative disorders associated with the deposition of fibrillary aggregates of a-syn within selective populations of neurones and glia. These deposits can be found within neuronal soma as Lewy bodies (LB) or in dystrophic neurites in diseases such as Parkinson's disease (PD) or Dementia with Lewy bodies (DLB); or in glial cytoplasmic inclusions in multiple system atrophy (MSA).[3]

The presence of a-syn has been detected in biological fluids such as cerebrospinal fluid (CSF)[4] and serum.[5] The measurement of a-syn concentrations in CSF by ELISAs has been proposed as a biomarker for a-syn related disorders. However, despite many studies showing a reduction in CSF a-syn levels in PD and in DLB[4,6], overall results are not consistent.[7] Even in those studies where a reduction in CSF a-syn has been demonstrated, the differences are small[8] and there is considerable overlap within patient groups and between patient and control groups. In addition the standardisation of CSF a-syn measurement between laboratories has proven difficult.[9]

The aggregation properties of a-syn have recently been compared to prion protein, the aggregation of which causes transmissible spongiform encephalopathies (TSEs).[10] Indeed, there is much discussion in current literature as to whether the alpha-synucleinopathies are actually prion-like diseases.[11] A recently-described technique called real-time quaking induced conversion (RT-QuIC), which exploits the ability of prion protein to induce self-aggregation, has been used to develop a diagnostic CSF test for sporadic Creutzfeldt-Jakob disease (sCJD), the most common human form of TSE.[12]

However, given the significant differences between prion proteins and a-syn, these techniques have failed to detect in any reliable way the presence of a-syn or a-syn aggregation in a biological sample. Therefore, there remains a need for a reliable assay to detect the presence of a-syn and a-syn aggregation in a biological sample.

At least one aim of the present invention is to provide an improved assay to detect the presence of a-syn and/or the aggregation of a-syn in a biological sample.

SUMMARY OF THE INVENTION

According to a first aspect of the invention there is provided a method of detecting the presence of alpha-synuclein aggregation in a biological sample, the method comprising the steps:
(i) providing a biological sample;
(ii) providing a reaction sample comprising a population of beads, a fluorophore adapted to bind to protein aggregates and to increase fluorescence when bound to protein aggregates, and alpha-synuclein or a fragment or variant thereof;
(iii) combining the biological sample and the reaction sample to form a reaction mixture;
(iv) incubating the reaction mixture with intermittent agitation cycles;
(v) illuminating the sample with a wavelength of light that excites the fluorophore of the reaction sample; and
(vi) determining the level of fluorescence of the reaction mixture during incubation,
wherein steps (iv) to (vi) are carried out at the same time, and a significant increase in the fluorescence of the reaction mixture during steps (iv) to (vi) is indicative of the presence of aggregates of alpha-synuclein in the reaction mixture, and wherein the presence of aggregates of alpha-synuclein in the reaction mixture is indicative of the presence of aggregates of alpha-synuclein in the biological sample.

The person skilled in the art will understand that the terms "alpha-synuclein", "a-syn", "a-synuclein", and "a-syn" refer to the alpha-synuclein protein and are used interchangeably throughout. For example, in embodiments where the biological sample is obtained from a human subject, the alpha-synuclein is human alpha-synuclein having the sequence SEQ ID NO.1:

SEQ ID NO.1:
MDVFMKGLSK AKEGVVAAAE KTKQGVAEAA
GKTKEGVLYV GSKTKEGVVH GVATVAEKTK
EQVTNVGGAV VTGVTAVAQK TVEGAGSIAA
ATGFVKKDQL GKNEEGAPQE GILEDMPVDP
DNEAYEMPSE EGYQDYEPEA

The term "fragment" with reference to alpha-synuclein is intended to mean either a polynucleotide of at least 10, 20, 30, 50, 100, 120, 130, or 140 contiguous nucleotides of the sequence of alpha-synuclein, or any integer there between; preferred fragments are those which are capable of aggregation under the conditions of the method of the invention. For example, the fragment may comprise the amino acid sequence 1-60 or 61-140 of the native alpha-synuclein sequence.

By "variant" with reference to alpha-synuclein is meant an alpha-synuclein protein with at least one amino acid substitution, insertion, and/or deletion in the peptide or polypeptide sequence or an alteration to a moiety chemically linked to the protein.

Conservative substitution: One or more amino acid substitutions (for example of 1, 2, 5 or 10 residues) for amino acid residues having similar biochemical properties. Typically, conservative substitutions have little to no impact on the activity of a resulting peptide or polypeptide. For example, a conservative substitution in alpha-synuclein may be an amino acid substitution that does not substantially affect the ability of the peptide to aggregate in the reaction conditions of the method of the invention. In a particular example, a conservative substitution in alpha-synuclein, is an amino acid substitution that does not significantly alter the ability of the protein to aggregate under the reaction conditions of the method of the invention. Screening of variants of alpha-synuclein can be used to identify which amino acid residues can tolerate an amino acid substitution.

In one example. the alpha-synuclein may be human alpha-synuclein and one conservative substitution may be included in the peptide, such as a conservative substitution in SEQ ID NO:1. In another example, 10 or fewer conservative substitutions are included in the peptide, such as five or fewer. A peptide or protein of the invention may therefore include 1, 2, 3, 4, 5, 6, 7, 8, 9, 10 or more conservative substitutions. A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using peptide synthesis methods, for example as known in the art.

Substitutional variants are those in which at least one residue in the amino acid sequence has been removed and a different residue inserted in its place. Examples of amino acids which may be substituted for an original amino acid in a protein and which are regarded as conservative substitutions include: Ser for Ala; Lys for Arg; Gln or His for Asn; Glu for Asp; Asn for Gin; Asp for Glu; Pro for Gly; Asn or Gin for His; Leu or Val for 11e; 11e or Val for Leu; Arg or Gin for Lys; Leu or 11e for Met; Met, Leu or Tyr for Phe; Thr for Ser; Ser for Thr; Tyr for Trp; Trp or Phe for Tyr; and 11e or Leu for Val.

In one embodiment, the substitutions are among Ala, Val, Leu and 11e; among Ser and Thr; among Asp and Glu; among Asn and Gln; among Lys and Arg; and/or among Phe and Tyr.

Further information about conservative substitutions can be found in, among other locations, Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988), WO 00/67796 (Curd et al.) and in standard textbooks of genetics and molecular biology.

Normally alpha-synuclein forms a stably folded tetramer that resists aggregation. However, it has been suggested that mutations in alpha-synuclein promote aggregation, and that these aggregates of alpha-synuclein are a primary building block of the fibrils that are believed to be involved in alpha-synucleinopathies such as Dementia with Lewy bodies and Parkinson's disease.

Therefore, the detection or determination of whether a biological sample comprises aggregates of alpha-synuclein may allow the detection of such pathologies without requiring invasive or expensive techniques, and may allow the detection of such pathologies before they would be possible using standard methods.

Assays such as real-time quaking induced conversion (RT-QuIC) have not to date been able to detect the presence of aggregates of alpha-synuclein. The inventors have surprisingly found that the modified RT-QuIC method of the invention allows the detection of alpha-synuclein at very high sensitivity and specificity, and allows alpha-synuclein aggregate related pathologies to be differentiated from other protein aggregate related pathologies.

By "significant increase in fluorescence" we refer to an increase in fluorescence of at least the mean relative fluorescence plus two times the standard deviation of the mean relative fluorescence of the negative controls or baseline fluorescence at a suitable time point, typically within 90-120 hours.

Typically, the biological sample is a bodily fluid sample. However, the biological sample may be a cell-based tissue sample. The biological sample may be taken from a subject for analysis using the method of the invention, to allow a health care practitioner to determine whether the subject may have a disease that is associated with the presence of aggregates of alpha-synuclein.

The bodily fluid may be selected from the group including cerebrospinal fluid, blood, or blood fractions, nasal fluid or tissue, urine, faeces, and lymph. Preferably, the bodily fluid is selected from the group including cerebrospinal fluid, blood plasma or other fraction, and nasal tissue or fluid. For example, the bodily fluid may be cerebrospinal fluid. In another example, the bodily fluid may be nasal tissue or fluid that has been extracted using a nasal swab, for example. In a further example, the bodily fluid may be a blood sample or blood fraction.

Accordingly, the method of the invention may allow the detection of a disease associated with aggregation of alpha-synuclein from a biological sample taken from a subject, allowing a non-invasive method of diagnosis or prognosis.

The biological sample is typically taken from a mammalian subject, preferably from a human subject. However, the biological sample may be taken from piscine, avian, reptilian or amphibian subject.

The reaction sample typically comprises a solvent. The solvent may be an aqueous solvent such that the reaction sample is an aqueous solution.

The reaction sample may be a buffered reaction sample to substantially maintain the pH of the reaction sample. For example, the reaction sample may comprise a biologically acceptable buffer such as tris(hydroxymethyl)aminomethane (TRIS), phosphate buffered saline (PBS), 4-(2-hydroxyethyl)-1-piperazineethanesulfonic acid (HEPES), Piperazine-N,N'-bis(2-ethanesulfonic acid) (PIPES), or Sorensen's phosphate buffer, for example.

Typically, the reaction sample is buffered to maintain the pH of the reaction sample from about pH 6 to about pH 8.5. Preferably, the reaction sample is buffered to maintain the pH of the reaction sample from about 7.0 to about 8.5. For example, the reaction sample may be buffered to maintain the pH of the sample at pH 7.0, 7.2, 7.4, 7.6, 7.8, 8.0, 8.2 or 8.4.

Preferably, the reaction sample is buffered to maintain a pH of less than a pH of 9.0.

Preferably, the reaction sample is buffered to maintain a pH of the reaction sample at pH 8.0, 8.2 or 8.4.

The fluorophore of the reaction sample typically changes fluorescence when bound to aggregates of protein. For example, the fluorophore may fluoresce weakly when free in solution and may fluoresce strongly when bound to protein aggregates. Alternatively, the fluorophore may not fluoresce when the fluorophore is free in solution and may fluoresce when the fluorophore is bound to protein aggregates.

The protein aggregates may comprise significant beta-sheet content, and the non-aggregated protein may lack significant beta-sheet content, and the fluorophore may be configured to bind to beta-sheets of protein.

The emission spectra of the fluorophore may shift when the fluorophore is bound to the aggregated protein. For example, the emission spectra of the fluorophore may be red-shifted when the fluorophore binds to the protein aggregates. Alternatively, the emission spectra of the fluorophore may be blue-shifted when the fluorophore binds to the protein aggregates.

Typically, the fluorophore is a thioflavin. Preferably, the fluorophore is thioflavin T (ThT).

Alternatively, the fluorophore may be cyanine T-284, or another fluorophore that increases fluorescence when bound to protein aggregates such as alpha-synuclein aggregates.

In standard RT-QuIC a small quantity of the protein that is to be aggregated is included in the reaction sample to act as a substrate for protein aggregation. Accordingly, the reaction sample may comprise less than 1 mg/ml alpha-synuclein to act as an aggregation substrate. The reaction sample may comprise less than 0.5 mg/ml alpha-synuclein. The reaction sample may comprise less than 0.1 mg/ml alpha synuclein.

The reaction sample may comprise from approximately 0.01 mg/mL alpha-synuclein to about 10 mg/mL alpha-synuclein to act as an aggregation substrate. The reaction sample may comprise from approximately 0.1 mg/mL to about 1 mg/mL alpha-synuclein to act as an aggregation substrate.

The alpha-synuclein of the reaction sample may be recombinant alpha-synuclein, from human or other species. The alpha-synuclein of the reaction sample may be a fragment of full length alpha-synuclein. For example, the fragment may comprise amino acids 1-60 or 61 to 140 of full length alpha-synuclein.

The beads of the population of beads of the reaction sample may comprise zirconia, silica, glass, quartz, or a polymer such as polystyrene, polytetrafluoroethylene (PTFE), polymethylmethacrylate (PMMA), or combinations thereof.

Typically, the population of beads have a mean diameter of the beads from approximately 1 mm to approximately 0.001 mm.

The mean diameter of the population of beads may be from approximately 1 mm to approximately 0.1 mm. For example, the mean diameter of the beads may be 1 mm, 0.5 mm or 0.1 mm.

The population of beads may have a standard distribution of diameters of approximately plus or minus 10% from the mean diameter. Accordingly, the diameter of the beads may be substantially homogeneous.

The reaction sample may comprise from approximately 1 mg to approximately 150 mg of beads per 100 μL of reaction mixture. The reaction sample may comprise from approximately 10 mg to approximately 100 mg of beads per 100 μL of reaction mixture. The reaction mixture may comprise approximately 10, 20, 30, 40 or 50 mg of beads per 100 μL of reaction mixture, or an amount there between. For example, the reaction mixture may comprise from about 10 to 50 mg of beads per 100 μL of reaction mixture, from 20 to 50 mg of beads per 100 μL of reaction mixture, or 30 to 50 mg of beads per 100 μL of reaction mixture.

The presence of aggregates of alpha-synuclein in the biological sample is indicative of a disease associated with the abnormal aggregation of alpha-synucein. For example, the disease may be Dementia with Lewy Bodies or Parkinson's disease, or other alpha-synucleinopathies.

The reaction mixture may be incubated for more than 40 hours, more than 60 hours, more than 80 hours, or more than 120 hours. The reaction mixture may be agitated for a period and allowed to stand for a period. Typically, the period within which the reaction mixture is agitated is significantly shorter than the period within which the reaction mixture is allowed to stand without agitation. The reaction mixture may be agitated for a period of at least 1 minute, at least 2 minutes, or at least 5 minutes. The reaction mixture may be allowed to stand for a period of at least 10 minutes, at least 15 minutes, or at least 20 minutes. For example, the reaction mixture may be agitated for a period of one minute, and allowed to stand without agitation for a period of fourteen minutes.

The intermittent agitation cycles may comprise intermittent shaking cycles. The shaking cycles may move the reaction mixture in a circular or orbital motion and therefore, the rate of shaking may be defined in terms of rotations per minute, for example. Alternatively, the shaking cycles may move the reaction mixture back and forth along a single axis, and therefore, the rate of shaking may be defined in terms of repetitions per minute.

The reaction mixture may be subjected to agitation at a fixed rate. In the following, the rate of agitation is expressed in rotations per minute, but can equally be applied to repetitions per minute for embodiments where the shaking follows a linear motion. The reaction mixture may be subjected to agitation at at least 100 rotations per minute. The reaction mixture may be subjected to agitation at at least 150 rotations per minute. The reaction mixture may be subjected to agitation at at least 200 rotations per minute. The reaction mixture may be subjected to agitation from at least 100 rotations per minute to at least 300 rotations per minute. The reaction mixture may be subjected to agitation from at least 150 rotations per minute to at least 250 rotations per minute. For example, the reaction mixture may be subjected to agitation at 150, 200 or 250 rotations per minute. Preferably, the reaction mixture is subjected to agitation at 200 rotations per minute.

The required rate of agitation of the reaction mixture may vary depending on the shaking orbital of the shaker. The required rate of agitation of the reaction mixture may vary depending on the biological sample used in the method. For example, in embodiments where the biological sample is a blood fraction such as platelets in plasma, for example, the reaction mixture may be agitated at a rate of 400, 600, 800, 900 or 1000 rotations per minute.

The intermittent agitation cycles may comprise intermittent sonication of the reaction mixture. Sonication of the reaction mixture may agitate the reaction mixture to promote aggregation. Alternative methods of agitating the reaction mixture may also be used.

The method of the invention may be carried out at a temperature of from 25° C. to 45° C. The method of the invention may be carried out at a temperature of from 30° C. to 40° C. For example, the method may be carried out at a temperature of 30° C., 32°C, 34° C., 36°C, 38° C. or 40° C., and values between.

In one embodiment, the method of the invention may be carried out at a temperature of about 30° C. In an alternative embodiment, the method of the invention may be carried out at a temperature of about 35° C., or about 37° C.

The biological sample may be treated prior to the method of the invention to concentrate the alpha-synuclein in the biological sample. The biological sample may be treated prior to the method of the invention to extract alpha-synuclein from a complex biological sample.

The biological sample may be treated with a population of beads. The beads may comprise a magnetic material. For example, the beads may comprise a paramagnetic material and the beads may allow the separation of material that specifically binds to the surface of the beads using externally applied magnetic fields to extract the beads from a complex mixture. The magnetic beads may allow the extraction or concentration of alpha-synuclein in a biological sample prior to the method of the invention.

For example, the beads may comprise superparamagnetic iron oxide, or another paramagnetic material and the alpha-synuclein may bind to the beads and the application of a magnetic field may allow the beads, and therefore the alpha-synuclein to be separated or concentrated in a biological sample.

In a second aspect of the invention, there is provided a method of diagnosing alpha-synucleinopathies, the method comprising the steps:
  (i) providing a biological sample from a subject;
  (ii) providing a reaction sample comprising a population of beads, a fluorophore adapted to bind to protein aggregates and to increase fluorescence when bound to protein aggregates, and alpha-synuclein or a fragment or variant thereof;
  (iii) combining the biological sample and the reaction sample to form a reaction mixture;
  (iv) incubating the reaction mixture with intermittent agitation cycles;
  (v) illuminating the sample with a wavelength of light that excites the fluorophore of the reaction sample; and
  (vi) determining the level of fluorescence of the reaction mixture during incubation,
wherein steps (iv) to (vi) are carried out at the same time, and a significant increase in the fluorescence of the reaction mixture during steps (iv) to (vi) is indicative of the subject having an alpha-synucleinopathy.

The alpha-synucleinopathy is typically, Parkinson's or Dementia with Lewy Bodies.

The invention extends in a third aspect to the provision of a kit of parts comprising an aqueous buffered solution, the aqueous buffered solution comprising a population of beads, a fluorophore and alpha-synuclein or a fragment or variant thereof.

The kit of parts may be used as the reaction sample for the methods of the first and second aspects.

Preferred and optional features for the first aspect of the invention are preferred and optional features for the second and third aspects.

BRIEF DESCRIPTION OF THE FIGURES

Embodiments of the present invention will now be described, by way of non-limiting example, with reference to the accompanying drawings.

DETAILED DESCRIPTION

Figure 1:
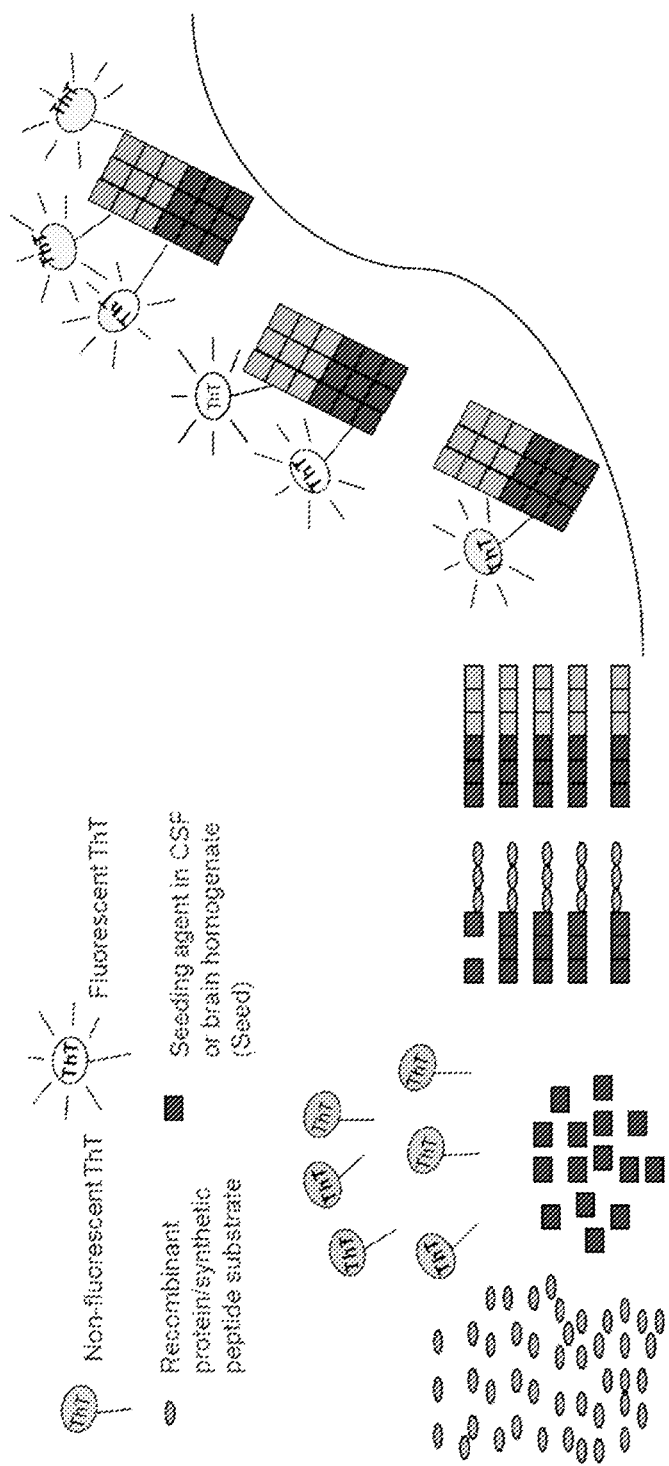
FIG. 1: A schematic diagram showing the process of standard RT-QuIC.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

General Materials and Methods

Real-Time Quaking Induced Aggregation for Alpha-Synuclein

The RT-QuIC reaction buffer (RB) was composed of 100 mM phosphate buffer (pH 8.2), 10 μM Thioflavin T (ThT) and 0.1 mg/ml human recombinant full-length (1-140aa) alpha-synuclein (Stratech, Cambridge, UK). Each well of a black 96-well plate with a clear bottom (Nalgene Nunc International, Fisher Scientific Ltd, UK) contained 98 μL, 90 μL or 85 μL RB (depending on volume of seed added) and 37+3 mg of 0.5 mm zirconium/silica beads (Thistle Scientific Ltd, Glasgow, UK). Reactions were seeded with 2 μL of working strength brain homogenate (BH), 5 μl, 10 μl or 15 μl of undiluted CSF to a final reaction volume of 100 μl. The plates were sealed with a plate sealer film (Fisher Scientific Ltd, UK) and incubated in a BMG OPTIMA FluoSTAR plate reader at 30° C. for 120 h with intermittent shaking cycles: double orbital with 1 minute shake (200 rpm), 14 minute rest. ThT fluorescence measurements (450 nm excitation and 480 nm emission) were taken every 15 minutes. Each sample was run in duplicate, allowing 2 negative control samples (reactions seeded with SD and AD BH), 1 positive control (reaction seeded with DLB BH), an unseeded reaction and 44 CSF samples to be tested on one plate.

Patient Groups

Initial phase of CSF RT-QuIC development was carried out on 99 CSF samples obtained from the OPTIMA cohort (Oxford Project to Investigate Memory and Ageing) with clinically and neuropathologically confirmed diagnosis of pure DLB (n=12), PD (n=2), progressive supranuclear palsy (PSP) (n=2), corticobasal degeneration (n=3), DLB with AD pathology (n=17), AD with incidental LBs (n=13), pure AD (n=30) and controls (n=20). OPTIMA initiated in 1988, is a prospective, longitudinal clinico-pathological study of dementia and aging including CSF collection at multiple time points during clinical follow-up. All clinical and pathological protocols have been described in detail[13] and were approved by the local ethics committee and participants provided informed consent prior to enrolment.

The validation phase of RT-QuIC was carried out on CSF samples (20 PD, 15 controls and 3 at-risk) obtained from the Oxford Discovery cohort, which is one of the largest, clinically best-characterized longitudinal PD cohorts to date. Full clinical details of this cohort have been described previously.[14] In brief, patients with idiopathic PD diagnosed within 3.5 years according to UK PD Society Brain Bank diagnostic criteria[15] were recruited between September 2010 and September 2014 from a 2.9 million population (ethics study 10/H0505/71). Mean disease duration among 20 PD patients was 1.6+1.1 years (range 0.1-3.2 years) and Hoehn and Yahr stage 1.9+0.4 (range 1-3, maximum possible score 5). The control population were recruited from spouses and friends of patients taking part in the study, as well as the general public. The at-risk group comprised patients with REM sleep behaviour confirmed on overnight polysomnography,16 80% of which have shown to develop Lewy body disorder over time.17 Demographic information is given in Table 1.

TABLE 1

Patient demographic information for the Optima and Discovery patients investigated

| | Age at death Mean ± SD (range) | F/M |
|---|---|---|
| OPTIMA patients (n) | | |
| Pure LBD (12) | 80.8 ± 6.5 (71-92) | 4/8 |
| Parkinson's disease (2) | 77.5 ± 7.8 (72-83) | 0/2 |
| Mixed LBD/AD (17) | 80.1 ± 6.4 (69-90) | 10/7 |
| AD with incidental LB (13) | 79.8 ± 7.8 (67-91) | 9/4 |
| Pure AD (30) | 77.7 ± 8.6 (61-93) | 17/13 |
| Progressive supranuclear palsy (PSP) (2) | 69.5 ± 3.5 (67-72) | 2/0 |
| Corticobasal degeneration (CBD) (3) | 64.0 ± 10.6 (52-72) | 1/2 |
| Controls (20) | 82.9 ± 6.9 (68-93) | 10/10 |
| Discovery patients (n) | | |
| Parkinson's disease (20) | 65.1 ± 9.1 (42-80) | 6/14 |
| At-risk RBD patients (3) | 67.6 ± 7.7 (59-74) | 0/3 |
| Controls (15) | 65.8 ± 7.4 (55-83) | 8/7 |

Brain Homogenates

Brain tissue was provided the MRC Brain Bank in the NCJDRSU (ethical licence 11/ES/0022). All tissue was frozen at −80° C. within 2 hours of being sampled and stored at −80° C. prior to analysis. Brain tissues had been stored between 2-18 years prior to use.

Frontal cortex tissue was taken from patients with Alzheimer's disease (AD); sporadic Creutzfeldt-Jakob disease (sCJD); and Diffuse Lewy body dementia (DLB). In addition frontal cortex was obtained from individuals without neurodegenerative disease from the MRC Sudden Death Brain and Tissue Bank (Sudden Death (SD) controls). Both frontal cortex and substantia nigra tissue was obtained from patients with mixed AD/DLB; mixed SCJD/DLB and mixed AD/PD. All cases used had been examined histologically and the diagnosis reached using internationally accepted criteria.[18] Initial 10% w/v brain homogenates (BH) were prepared using phosphate buffered saline (PBS) containing 1 mM EDTA, 150 mM NaCl, 0.5% Triton X and complete protease inhibitor cocktail from Roche. Subsequent working strength BHs were prepared by diluting the above 1:20,000 with PBS.

Cerebrospinal Fluid Samples

CSF samples were stored in 0.5 mL aliquots in polypropylene tubes at −80° C. prior to analysis. 99 CSF samples from the OPTIMA cohort and 38 CSF samples from the Oxford Parkinson's Disease Centre (OPDC) Discovery study were received from the Nuffield Department of Clinical Neurosciences, University of Oxford. All CSF samples were transported from Oxford to Edinburgh on dry-ice and stored at −80° C. on arrival. In addition, CSF samples from patients with neuropathologically confirmed sCJD or DLB from the NCJDRSU CSF Bank were analysed. Ethical approval for the use of CSF samples from the NCJDRSU CSF Bank was covered by Multi-centre Research Ethics Committee for Scotland 05/MRE00/67. All CSF were spun and stored at −80° C. prior to analysis.

Results

Figure 2:
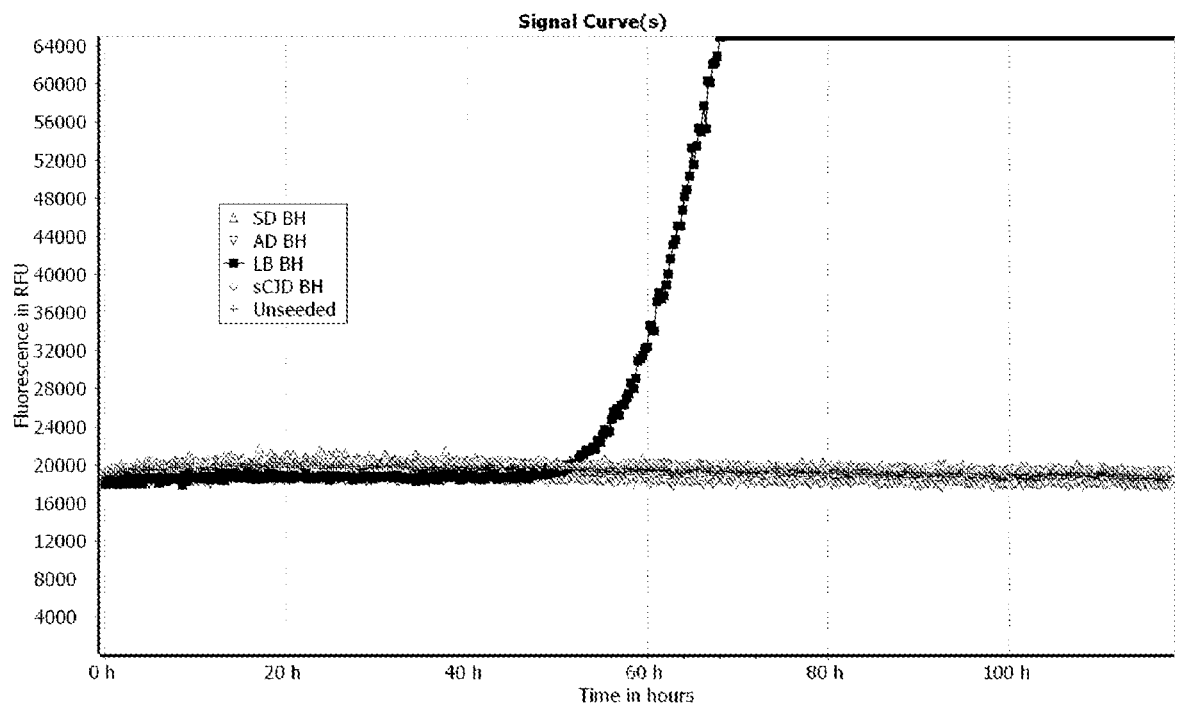
FIG. 2: RT-QuIC traces for brain homogenate (BH) samples from patients with Dementia with Lewy Bodies (DLB), Alzheimer's disease (AD) and sporadic Creutzfeldt-Jakob disease (sCJD) with patients with no neuropathological evidence of disease who died suddenly (SD) as controls.

The development of RT-QuIC was undertaken using frontal cortex BH from patients with a clinico-pathological diagnosis of DLB, Alzheimer's disease (AD) and sCJD. Patients with no neuropathological evidence of neurological disease who died suddenly and were part of the MRC Sudden Death brain bank were used as controls (SD) (FIG. 2). The RT-QuIC reactions seeded with BH from DLB had a lag-phase of 50 hours, after which an increasing thioflavine T fluorescent signal was seen that became maximal at 70 hours. None of the reactions seeded with BH from patients with other protein misfolding disorders (AD or sCJD) or the SD controls, gave a positive response even after 120 hours.

Figure 3:
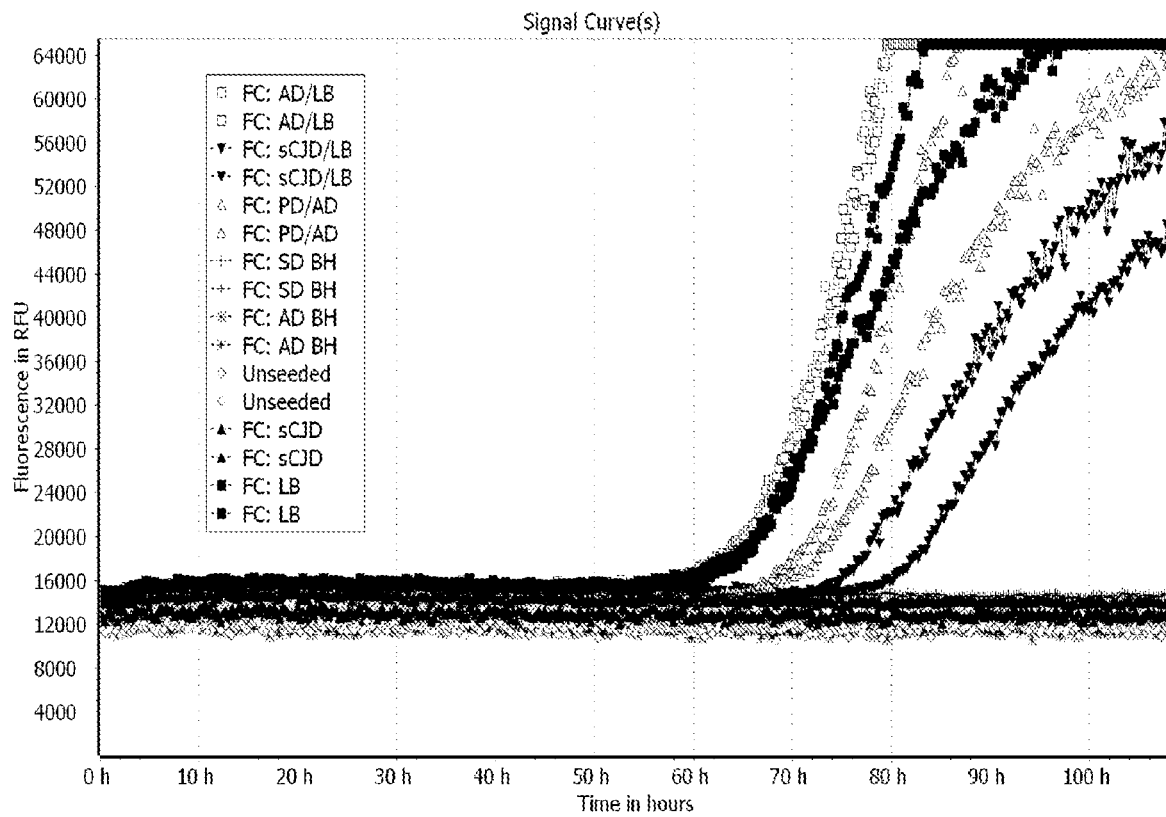
FIG. 3: RT-QuIC traces for BH samples from patients with mixed pathologies.
Figure 4:
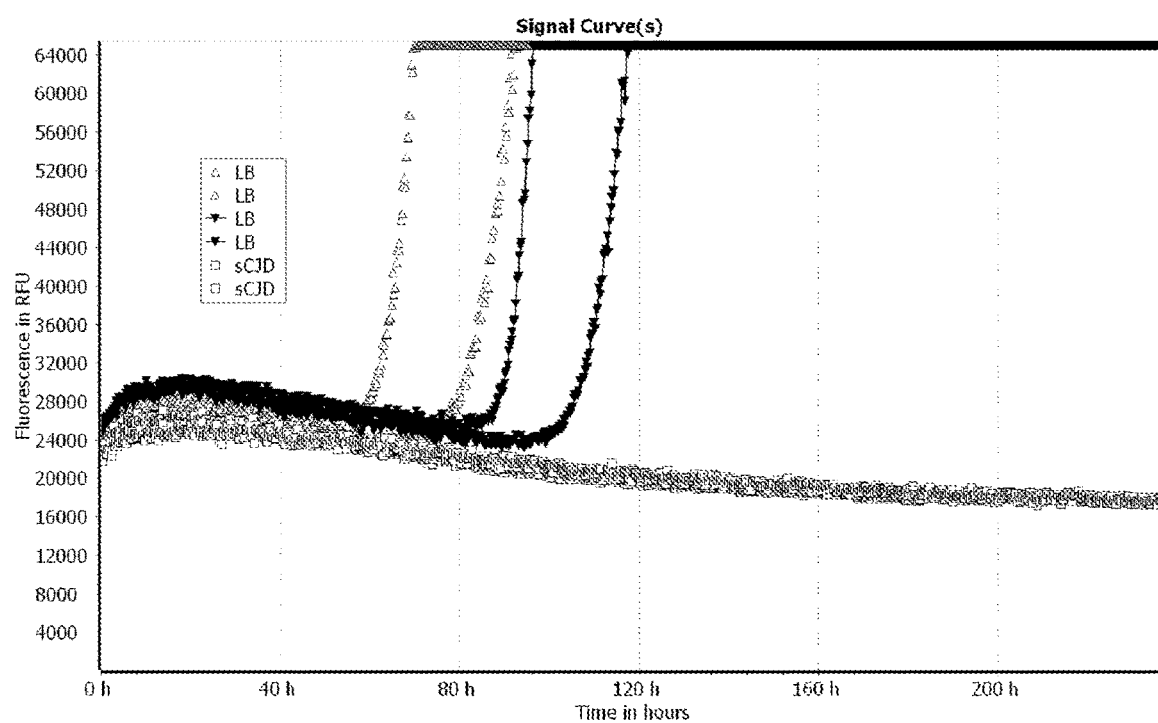
FIG. 4: RT-QuIC traces for cerebrospinal fluid (CSF) samples from confirmed DLB and sCJD patients.

Many disease pathologies commonly co-exist, especially AD-related and a-syn pathology[19]. To investigate whether the presence of an alternative protein-misfolding disorder can interfere with the a-syn aggregation induced by either DLB or PD, BHs from the frontal cortex of patients with mixed pathologies were examined (FIG. 3). The presence of a second protein-misfolding disorders such as AD or sCJD does not inhibit the RT-QuIC reaction induced by DLB or PD BHs (FIGS. 2 and 3). To investigate whether the RT-QuIC method developed was sensitive enough to detect a-syn in CSF, two CSF samples from patients with neuropathologically confirmed DLB and 1 CSF from a neuropathologically confirmed case of sCJD were analysed (FIG. 4). Both CSF samples from the DLB patients gave positive responses with a lag-phase between 60-100 hours.

Figure 5:
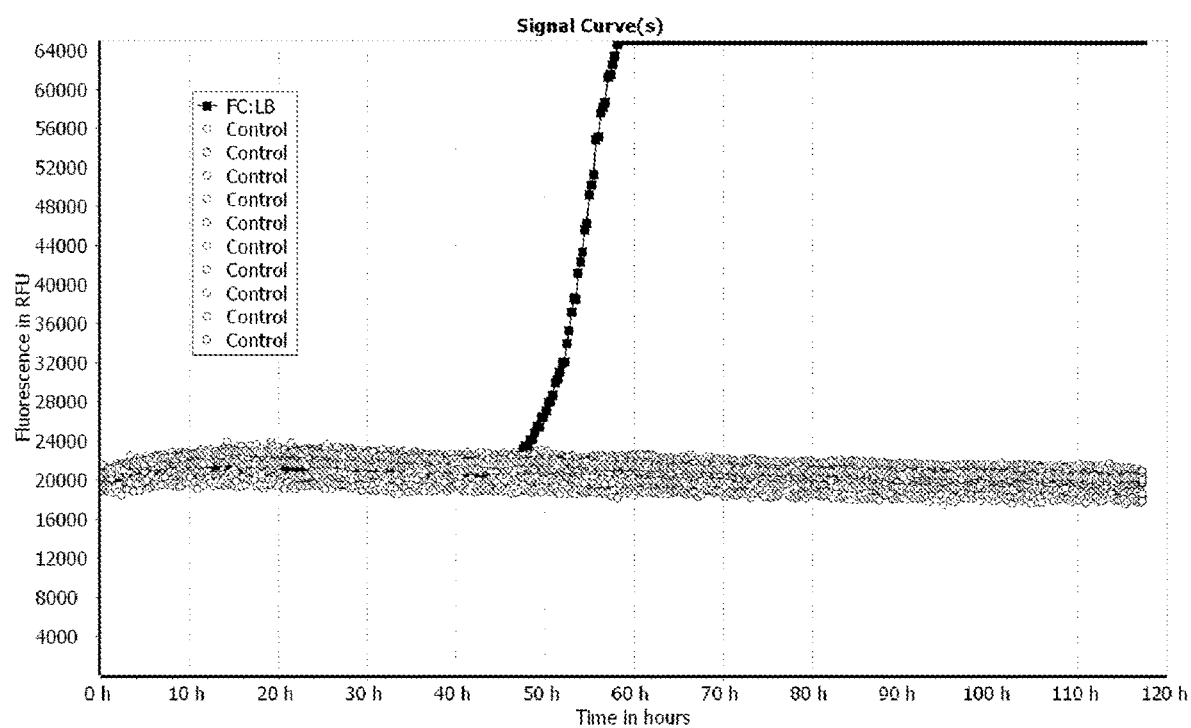
FIG. 5: RT-QuIC traces for control CSF samples and one BH sample from a patient with DLB.
Figure 6:
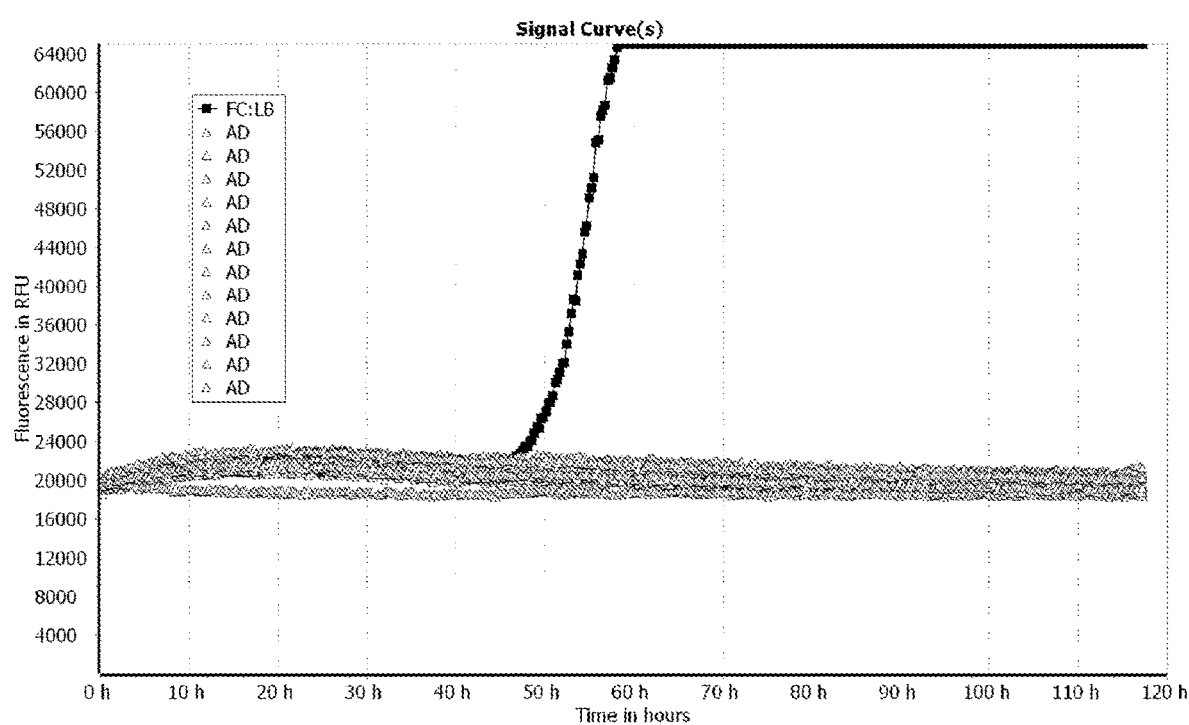
FIG. 6: RT-QuIC traces for CSF samples from patients with AD and one BH sample from a patient with DLB.
Figure 7:
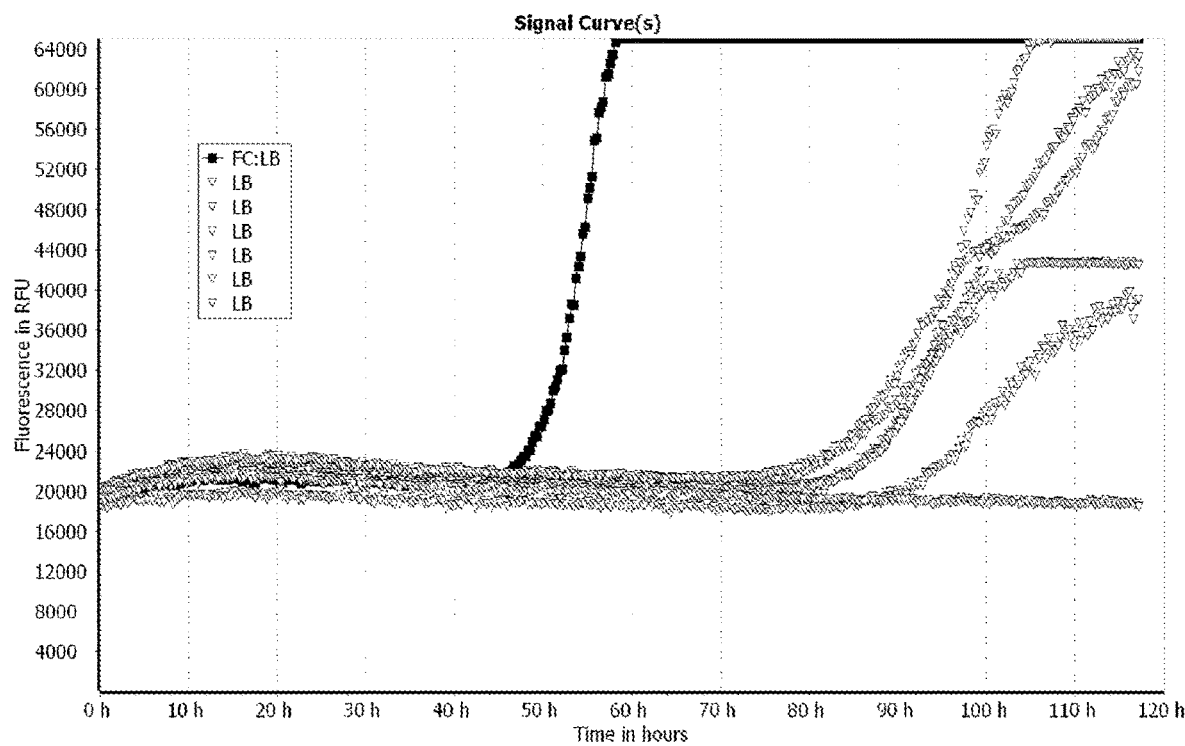
FIG. 7: RT-QuIC traces for CSF samples from patients with DLB and one BH sample from a patient with DLB.
Figure 8:
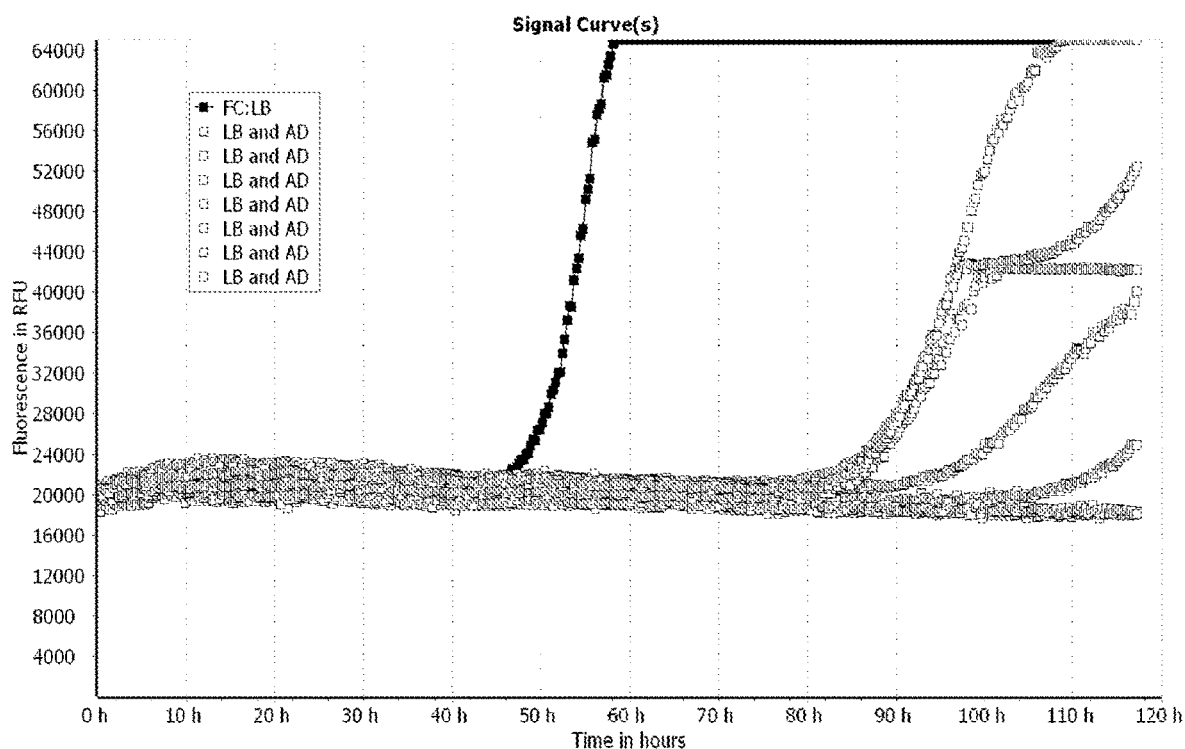
FIG. 8: RT-QuIC traces for CSF samples from patients with DLB and AD and one BH sample from a patient with DLB.

An exploratory set of 99 in vivo CSF samples obtained as part of the OPTIMA study from patients with subsequent neuropathologically confirmed disease were analysed at three different volumes (i.e. 5, 10 and 15 µl) to investigate the sensitivity and specificity of the RT-QuIC and to calculate the optimal CSF volume for the analysis (Table 2). Using a volume of 15 µl a sensitivity of 92% was obtained for CSF samples from DLB (FIGS. 7 and 8) and a sensitivity of 65% was obtained for CSF samples from patients with mixed DLB/AD pathology. None of the CSF samples from the control subjects (FIG. 5) or patients with pure AD (FIG. 6), CBD or PSP were positive. Using this exploratory set of CSF samples a positive response was defined as a relative fluorescence unit (rfu) value of >2SD above the mean of the negative controls at 120 hours of at least one of the CSF duplicates.

TABLE 2

Positive RT-QuIC reactions seeded with CSF samples from patients with neuropathologically confirmed DLB, mixed DLB/AD, AD with incidental LB, AD, PD and healthy controls (Exploratory Group) and patients with clinically diagnosed PD, at risk-PD, neuropathologically confirmed corticobasal degeneration and supranuclear palsy and PD controls (Confirmatory Group). A positive RT-QuIC response was classified as a relative fluorescence unit (rfu) value of >2 SD above the mean of the negative controls at 120 hours of at least one of the CSF duplicates.

| Exploratory Patient Group (n) | Number of Positive RT-QuIC (%) using 5 µl | Number of Positive RT-QuIC (%) using 10 µl | Number of Positive RT-QuIC (%) using 15 µl |
|---|---|---|---|
| AD with incidental LB (13) | 2 (15%) | 4 (31%) | 2 (15%) |
| Healthy Controls (20) | 0 (0%) | 0 (0%) | 0 (0%) |
| Mixed DLB/AD (17) | 9 (53%) | 11 (65%) | 11 (65%) |
| Parkinson's disease (2) | 2 (100%) | 2 (100%) | 2 (100%) |
| Progressive Supranuclear Corticobasal degeneration (3) | 0 (0%) | 0 (0%) | 0 (0%) |
| Pure AD (30) | 2 (7%) | 1 (3%) | 0 (0%) |
| Pure DLB (12) | 10 (83%) | 11 (92%) | 11 (92%) |
| Sensitivity (DLB) | 83% | 92% | 92% |
| Specificity (vs controls) | 100% | 100% | 100% |
| Specificity (vs AD) | 93% | 97% | 100% |
| Specificity (vs Controls + AD) | 96% | 98% | 100% |

| Confirmatory Patient Group (n) | | | Number of Positive RT-QuIC (%) using 15 µl |
|---|---|---|---|
| Parkinson disease (20) | / | / | 19 (95%) |
| At-risk PD patients (3) | / | / | 3 (100%) |
| Parkinson's disease controls | / | / | 0 (0%) |
| Sensitivity (PD) | / | / | 95% |
| Specificity | / | / | 100% |

Figure 9:
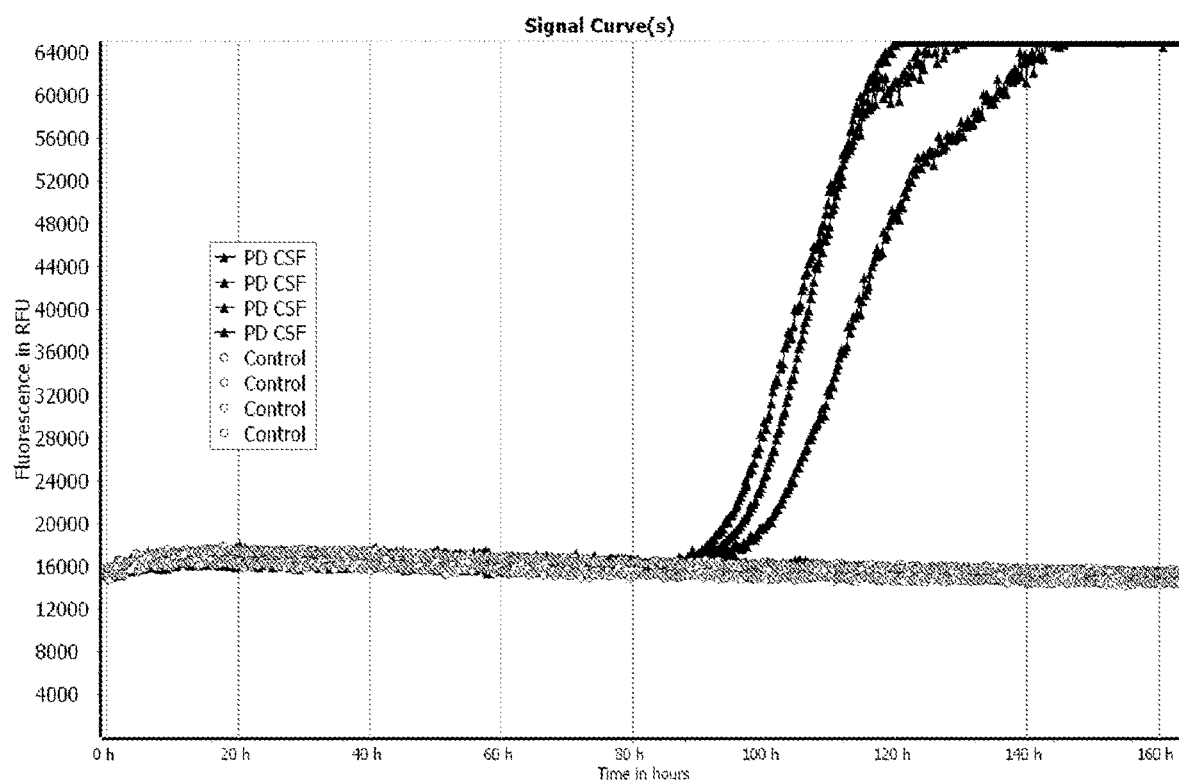
FIG. 9: RT-QuIC traces for CSF samples from patients with Parkinson's Disease (PD) and CSF samples from control subjects.
Figure 10:
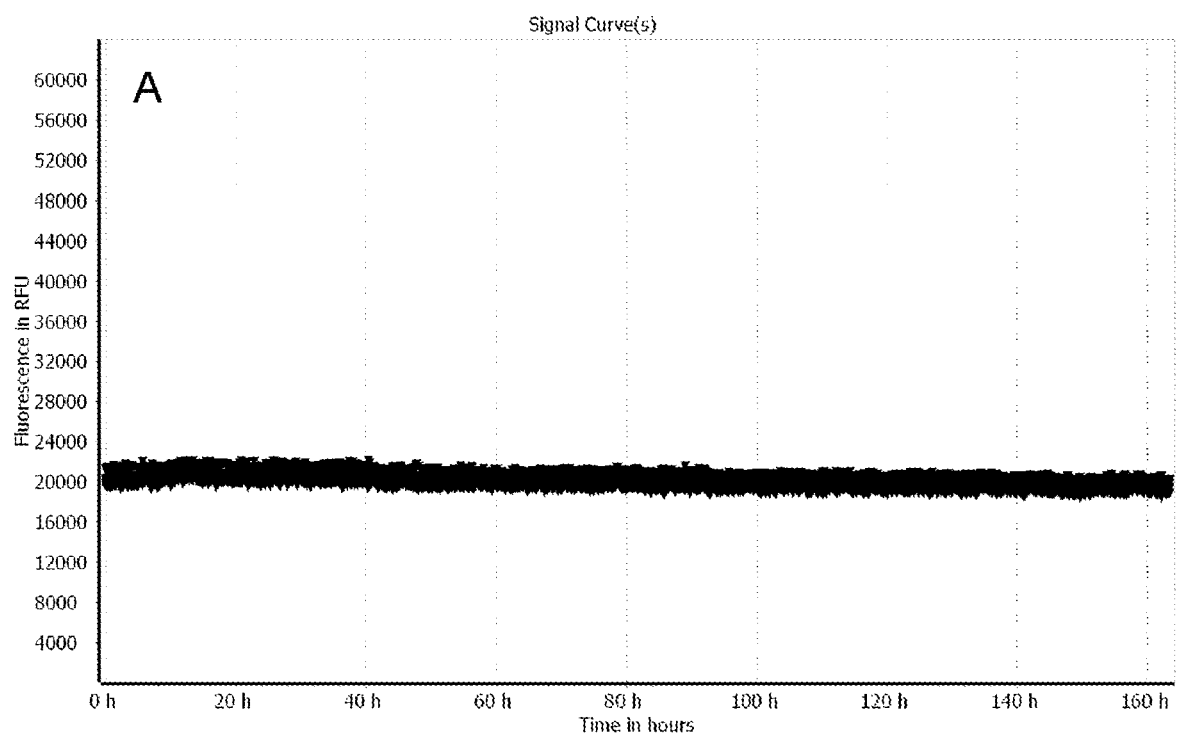
FIG. 10: RT-QuIC traces for SD BH samples A) with beads and B) without beads.
Figure 10:
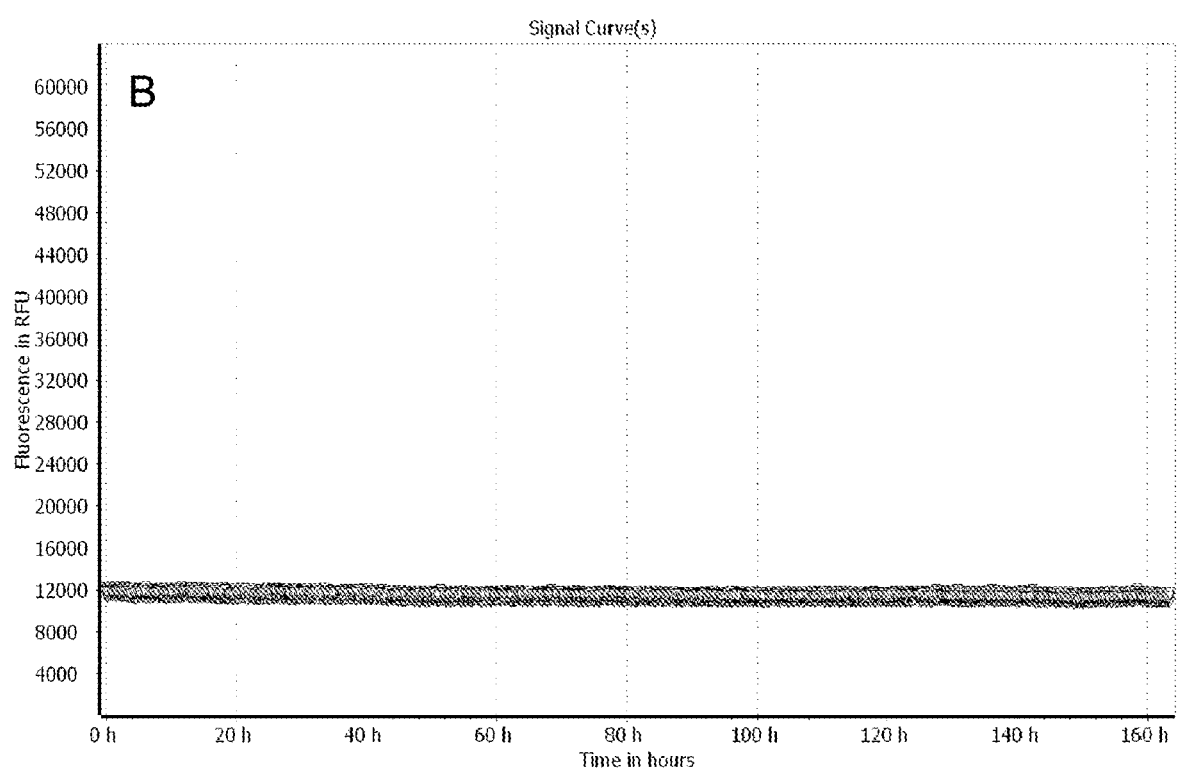
Figure 11:
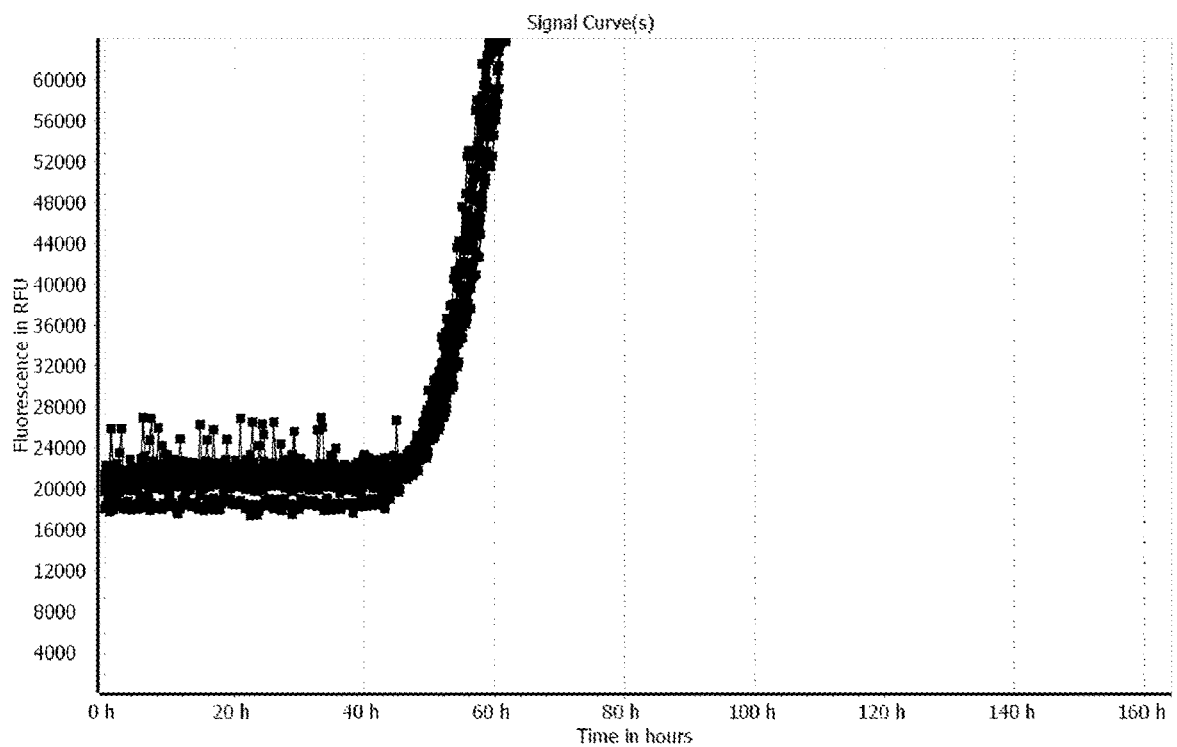
FIG. 11: RT-QuIC traces for DLB BH samples A) with beads and B) without beads.
Figure 11:
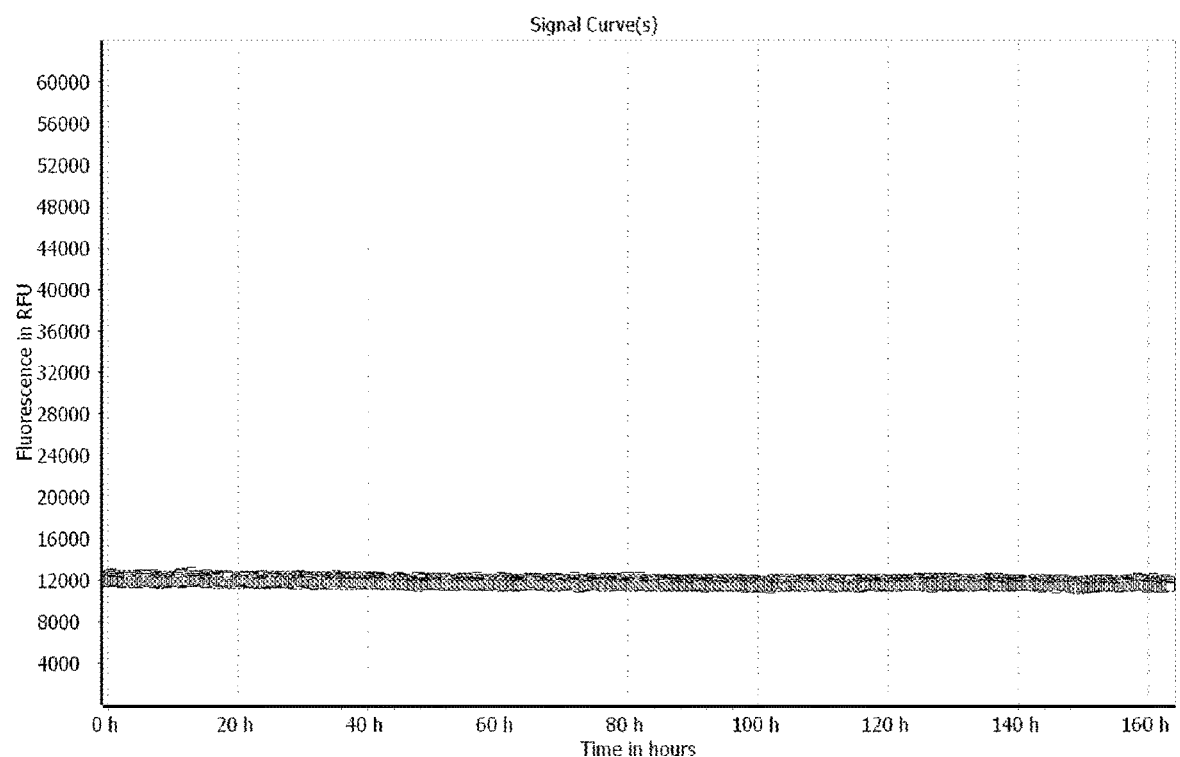
Figure 12:
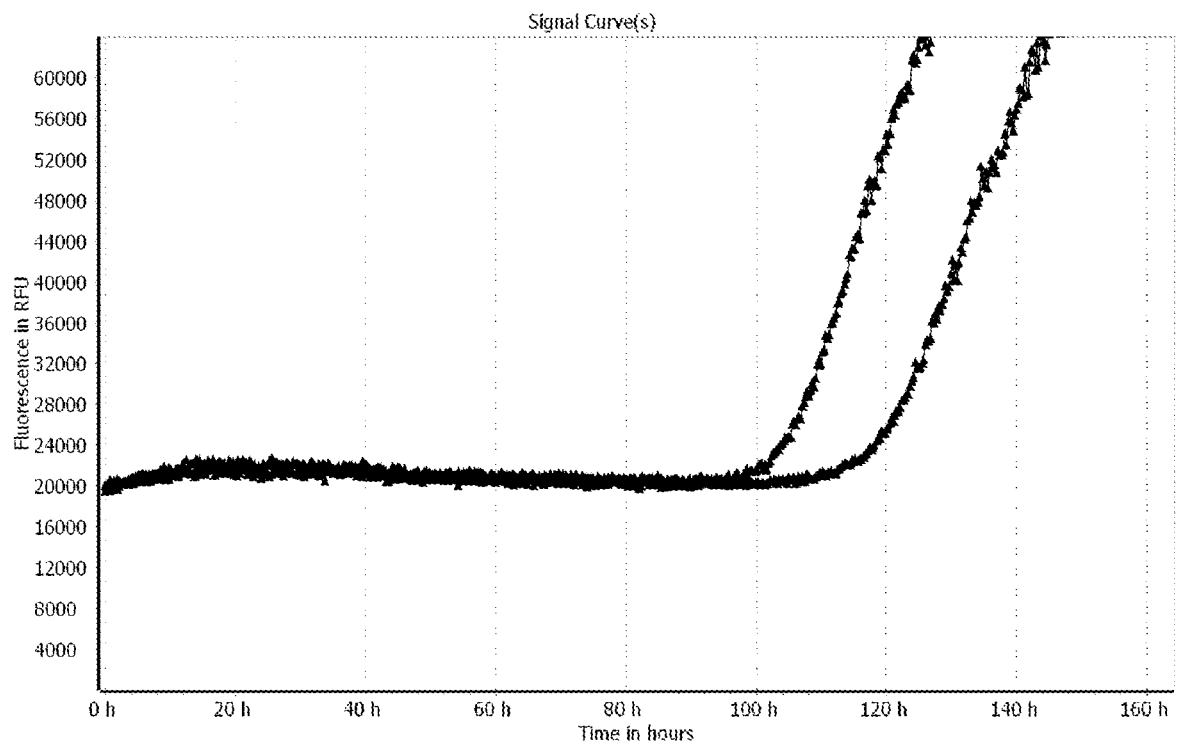
FIG. 12: RT-QuIC traces for Parkinson's Disease cerebrospinal fluid (CSF) samples A) with beads and B) without beads.
Figure 12:
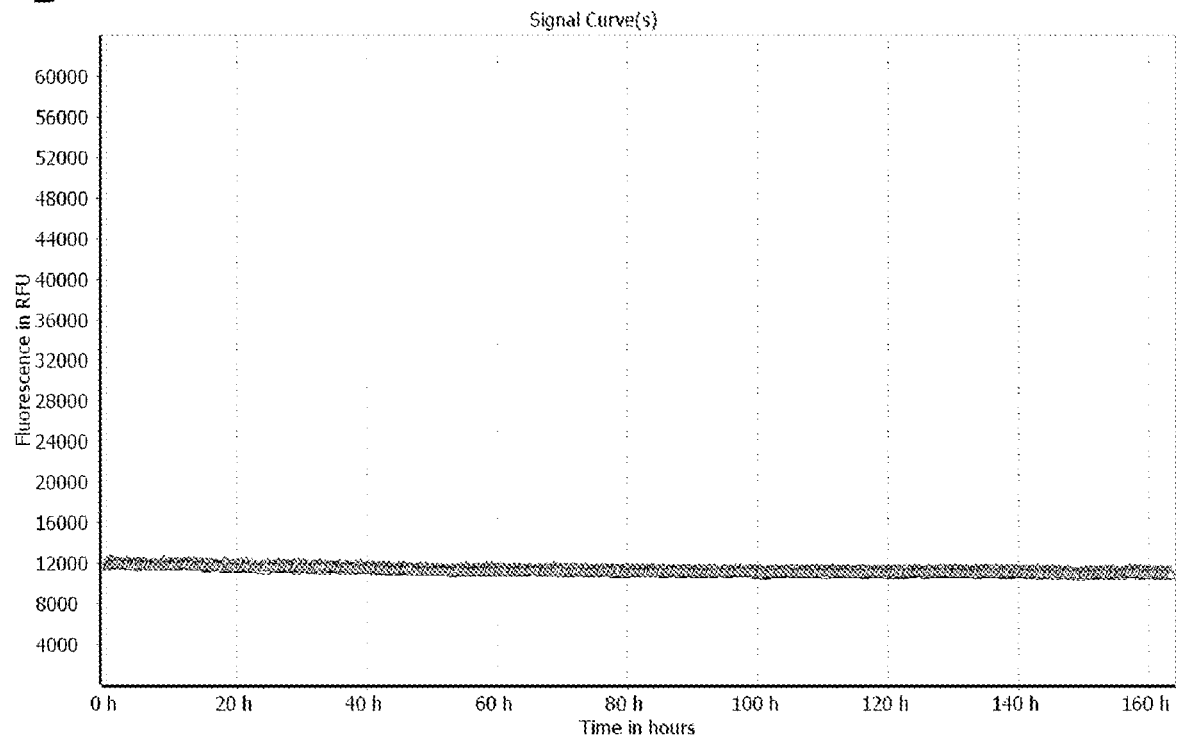
Figure 13:
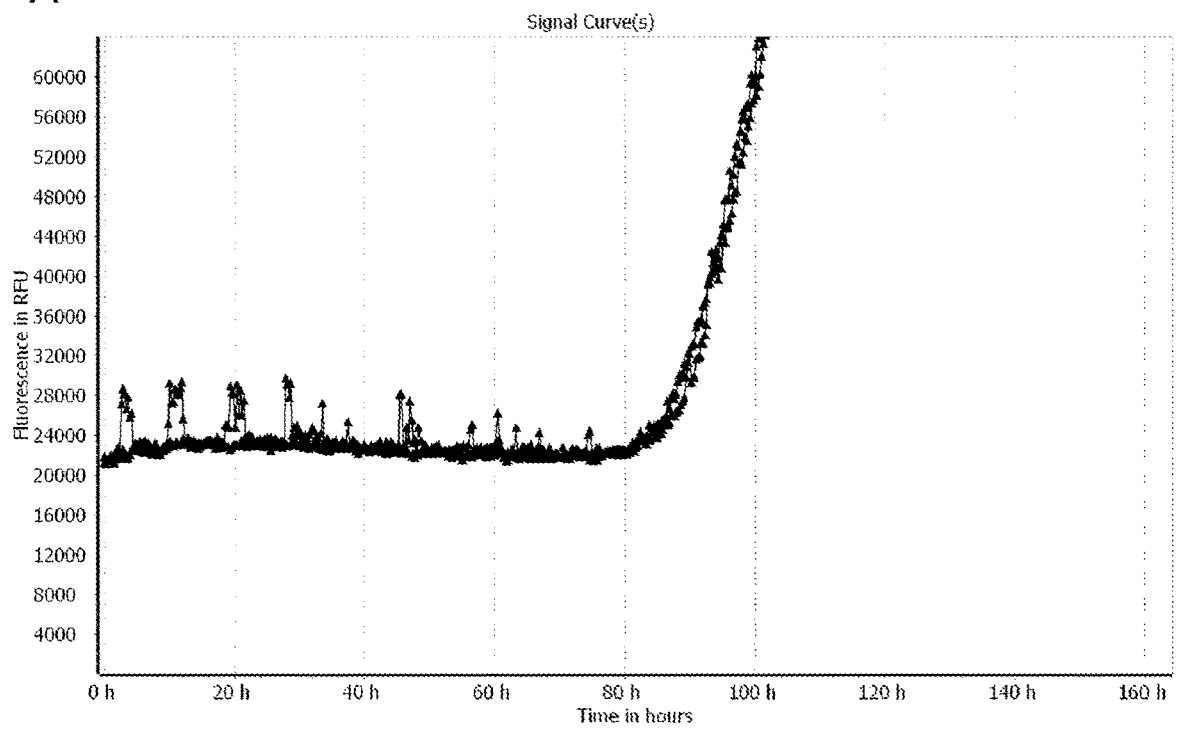
FIG. 13: RT-QuIC traces for Dementia with Lewy Bodies CSF samples A) with beads and B) without beads.
Figure 13:
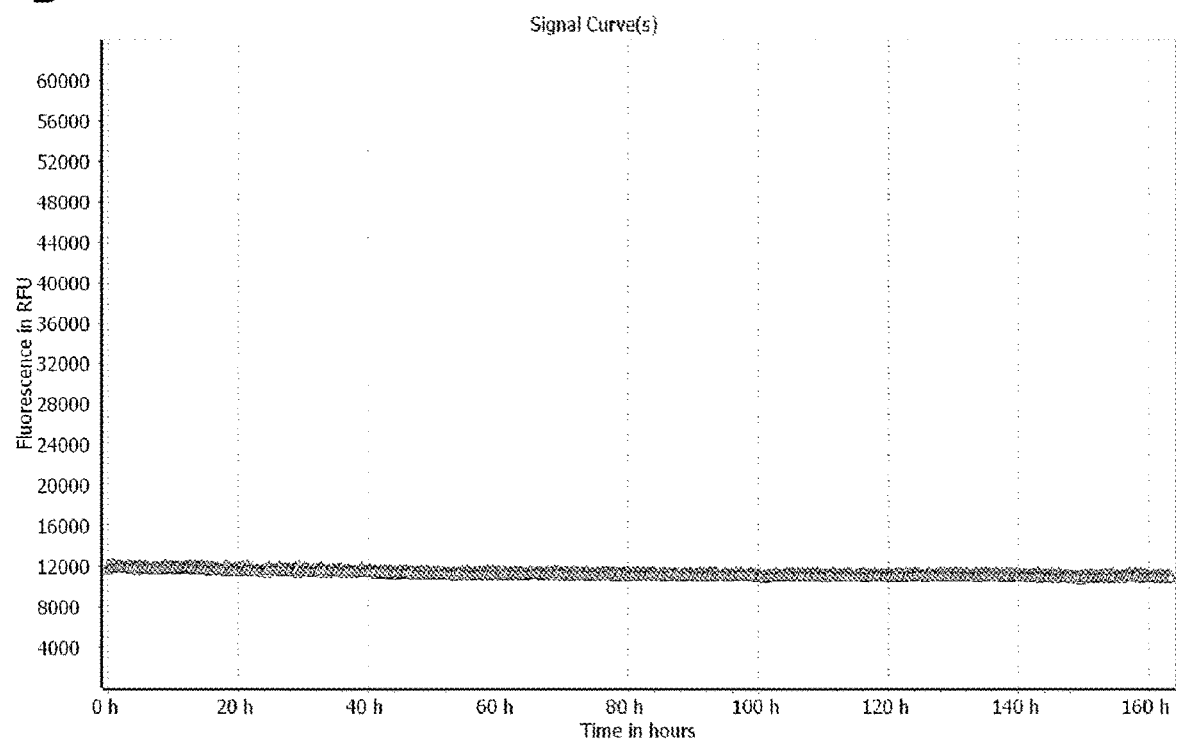

The second phase of the study was to apply these analytical conditions and cut-off criteria to a set of confirmatory in vivo CSF samples from 20 patients with clinically diagnosed PD, 15 control patients and 3 patients with REM sleep behaviour disorder (RBD) recognised to be at high risk of developing future alpha-synucleinopathies,[20] obtained from the large prospective, OPDC Discovery cohort[20]. These CSF samples were coded, analysed and reported without prior knowledge of the final diagnosis. After the samples were de-coded the results showed that 19 of the 20 PD patients had a positive RT-QuIC response (FIG. 9) and none of the 15 controls were found to be positive. This resulted in a RT-QuIC sensitivity and specificity for PD of 95% and 100% respectively (Table 2). Interestingly, all three patients at-risk of developing PD had a positive RT-QuIC response. These patients had RBD, of whom 80% have been shown to progress to develop a Lewy body disorder.[20]

DISCUSSION

The early diagnosis of both DLB and PD is hampered by the lack of sensitive and reliable clinical diagnostic tests. Both conditions are underpinned by the neuropathological deposition of an aggregated form of a-syn which is released into the CSF. We have exploited the ability of the aggregated a-syn to induce further aggregation of non-aggregated a-syn in a cyclical manner to develop a technique that can detect abnormal CSF a-syn in DLB and PD with a sensitivity of 92% and 95% respectively with 100% specificity. Uniquely, we found that 3 RBD patients at high future risk of developing a Lewy body disorder gave a positive RT-QuIC response, suggesting that this test could be used as an early diagnostic test for prodromal PD. Future work focusing on test validation in a larger cohort of RBD patients, followed by ongoing longitudinal assessment, will test the assay's utility in risk-stratifying those prodromal individuals most at risk of early PD conversion in whom neuroprotective therapies might be trialed. We also found that CSF samples from CBD and PSP patients do not give positive RT-QuIC responses. These are movement disorders associated with abnormalities in tau protein rather than a-syn which may be mistaken for PD in the early stages. Therefore, RT-QuIC offers a new approach to the detection of abnormal a-syn and one which has the potential to improve the early clinical diagnosis of PD and DLB in addition to other alpha-synucleinopathies such as MSA.

The Role of Beads in a Modified RT-QuIC Assay for the Detection of Alpha-Synuclein With reference to FIGS. 10-13, to show the role being played by the beads used in the above assays. parallel assays were carried out for Sudden Death (SD) Brain Homogenate (BH) samples A) with beads and B) without beads, Dementia with Lewy Bodies BH samples A) with beads and B) without beads, Parkinson's Disease cerebrospinal fluid (CSF) samples A) with beads and B) without beads, and Dementia with Lewy Bodies CSF samples A) with beads and B) without beads. These assays were carried out using the same general method described above. As can be seen from FIG. 10, no reading was seen for the SD samples. In addition, those samples with Lewy Body Disease and Parkinson's Disease without beads (FIG. 11B, FIG. 12B or FIG. 13B) showed no reading. However, readings are clearly seen for those samples with either Lewy Body Disease or Parkinson's Disease with the beads. Therefore, the presence of the beads is vital to the ability to detect the presence of a-syn aggregates using RT-QuIC.

Figure 14:
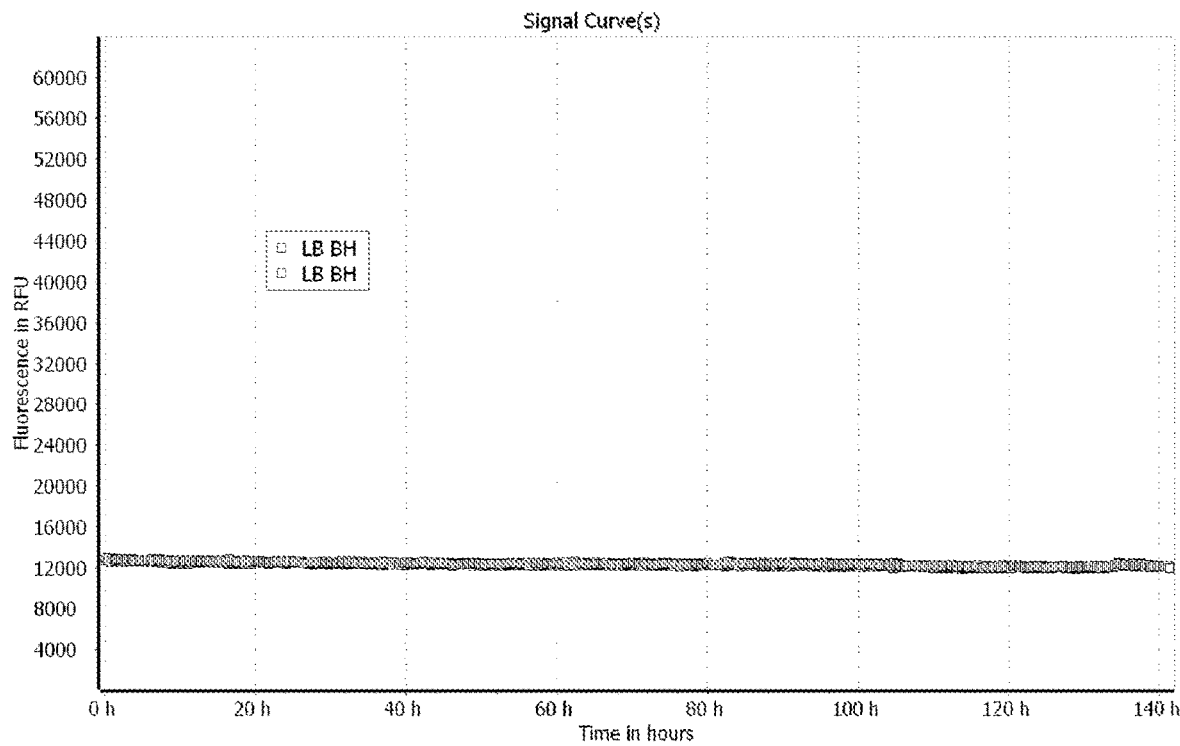
FIG. 14: RT-QuIC traces for Dementia with Lewy Bodies BH samples with A) no beads B) 18.7 mg beads per well and C) 37.5 mg beads per well.
Figure 14:
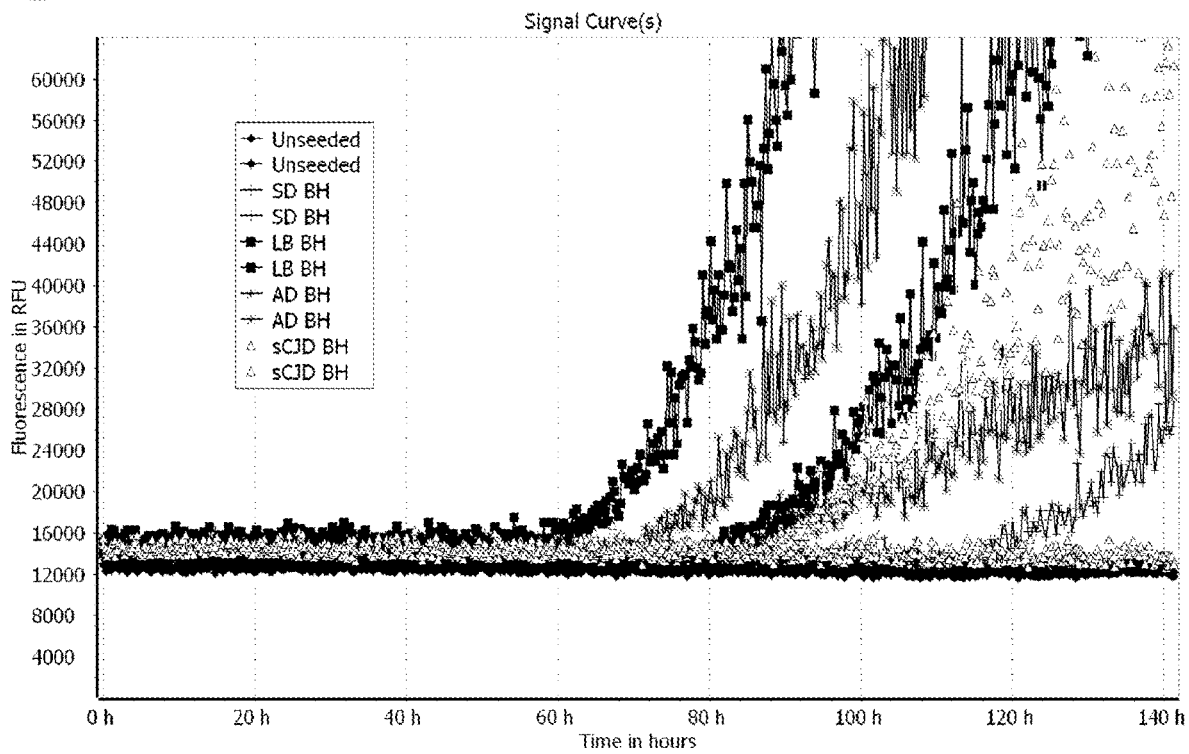
Figure 14:
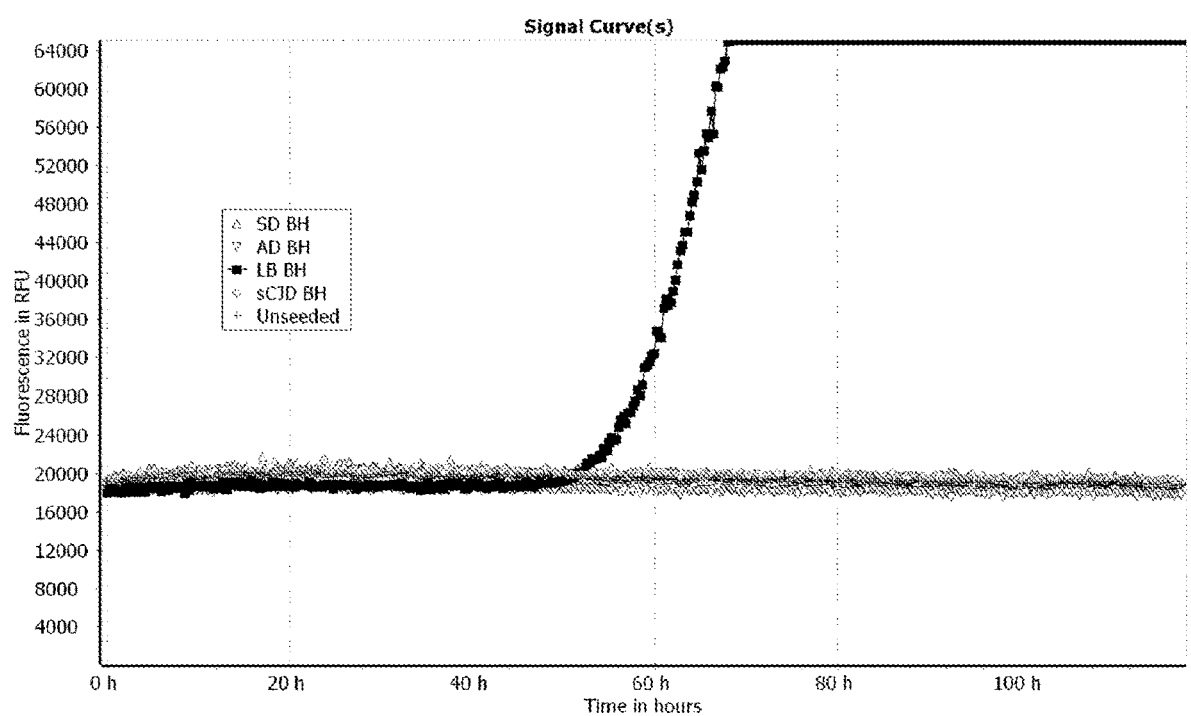

With reference to FIG. 14, the effect of bead concentration was investigated using Dementia with Lewy Bodies brain homogenate samples. Samples with no beads present in the reaction mixture showed a constant fluorescent signal, indicated a negative RT-QuIC result. In contrast, samples with 18.7 mg beads per well and 37.5 mg beads per well gave a clear increase in fluorescence and the higher concentration of beads giving a clearer and earlier signal.

Therefore it is clear the presence of the beads in the reaction mixture is crucial for a signal for the detection of alpha-synuclein aggregates to be obtained.

1. A-Syn RT-QuIC Reactions Using 0.1 mm, 0.5 mm and 2.3 mm Zirconium/Silica Beads (Approx.37+3 mg) and Seeded with BHs RT-QuIC reactions with the addition of 37 mg of 0.1 mm, 0.5 mm or 2.3 mm beads were seeded with 5 μL of 1:200,000 dilution of identical BH from control subjects (SDBH), Lewy body disease patients (LBDBH), Alzheimer's Disease (ADBH) or sporadic Creutzfeldt-Jakob disease (sCJDBH) or unseeded. The a-syn RT-QuIC responses obtained with 0.1 mm zirconium/silica beads are shown in FIG. 15A, those with 0.5 mm zirconium/silica beads are shown in FIG. 15B and those with 2.3 mm zirconium/silica beads are shown in FIG. 15C.

It can be seen from FIGS. 15A,B,C that increasing the size of the zirconium/silica beads results in an increase in the time taken to illicit a positive a-syn RT-QuIC response with LBDBH seeded reactions. However despite having a quicker response time using 0.1 mm zirconium/silica beads, the a-syn RT-QuIC gave positive reactions with ADBH seeded reactions.

2. A-Syn RT-QuIC Reactions Using 0.1 mm, 0.5 mm and 2.3 mm Zirconium/Silica Beads (Approx.37+3 mg) and Seeded with CSF Samples RT-QuIC reactions with the addition of 37 mg of 0.1 mm, 0.5 mm or 2.3 mm beads were seeded with 15 μL CSF samples from patients with Lewy Body disease (LB) or from control subjects. The a-syn RT-QuIC responses obtained with 0.1 mm zirconium/silica beads are shown in FIG. 16A, those with 0.5 mm zirconium/silica beads are shown in FIG. 16B and those with 2.3 mm zirconium/silica beads are shown in FIG. 16C.

The use of 0.1 mm and 0.5 mm zirconium/silica beads resulted in positive a-syn RT-QuIC reactions seeded with LB CSF samples but not with control CSF samples. In contrast the use of 2.3 mm zirconium/silica beads did not support a-syn RT-QuIC reactions seeded with CSF samples from LB patients. Identical CSF samples were used in the experiments illustrated in FIGS. 16A, B and C.

Figure 15:
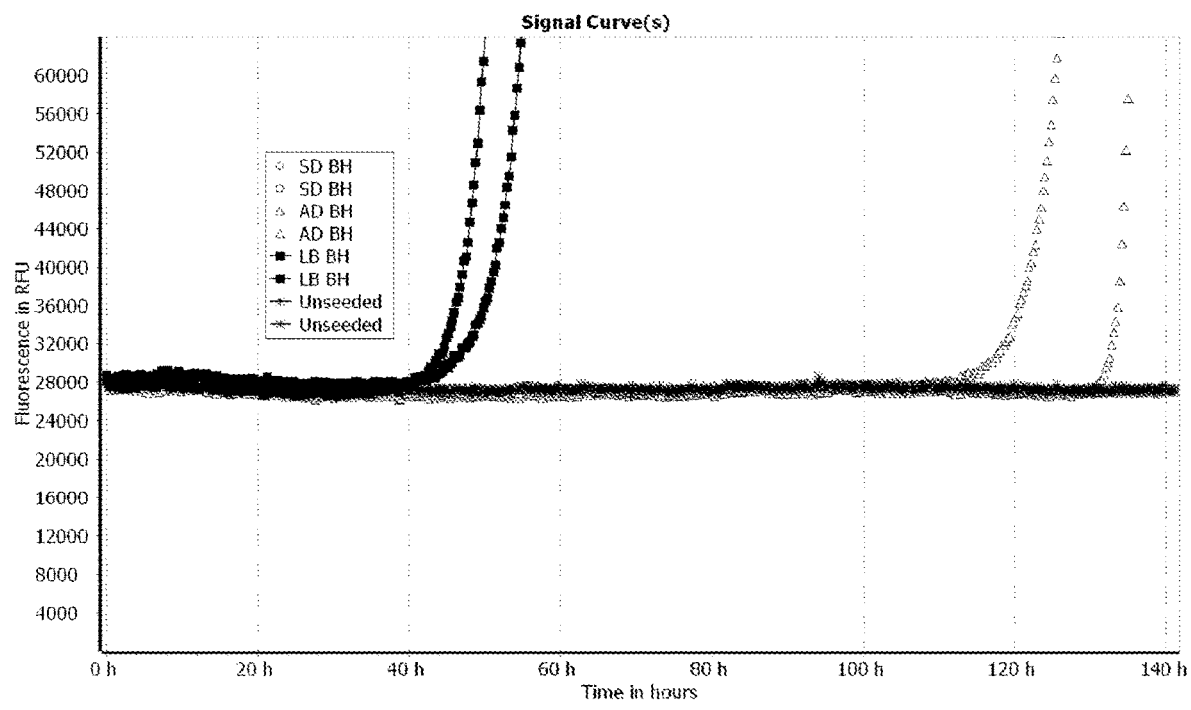
FIG. 15: RT-QuIC traces for BH from control subjects (SDBH), Lewy body disease patients (LBDBH), Alzheimer's Disease (ADBH) or sporadic Creutzfeldt-Jakob disease (sCJDBH) or unseeded for (A) 0.1 mm zirconium/silica beads, (B) 0.5 mm zirconium/silica beads and (C) 2.3 mm zirconium/silica beads.
Figure 15:
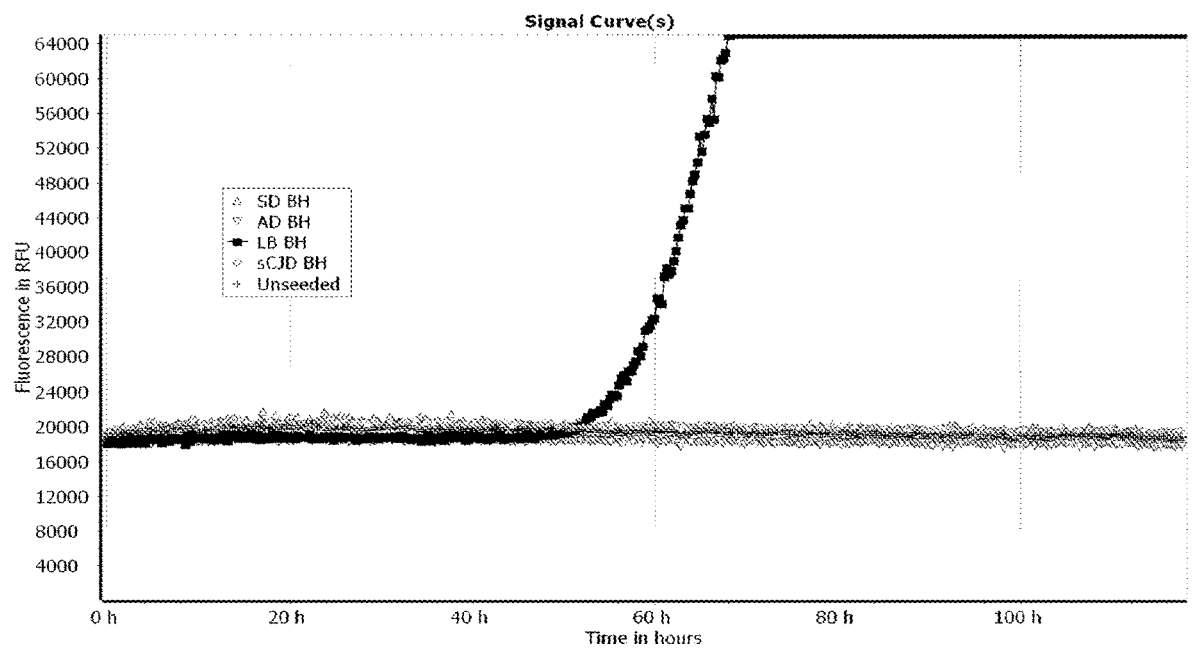
Figure 15:
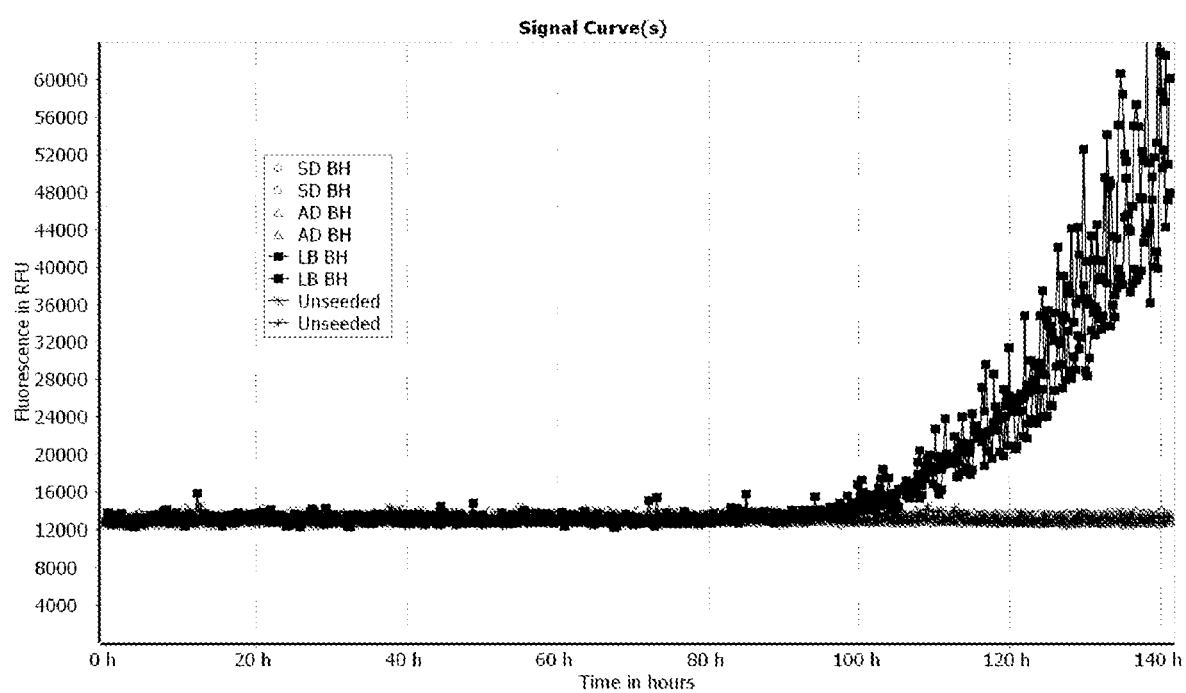
Figure 16:
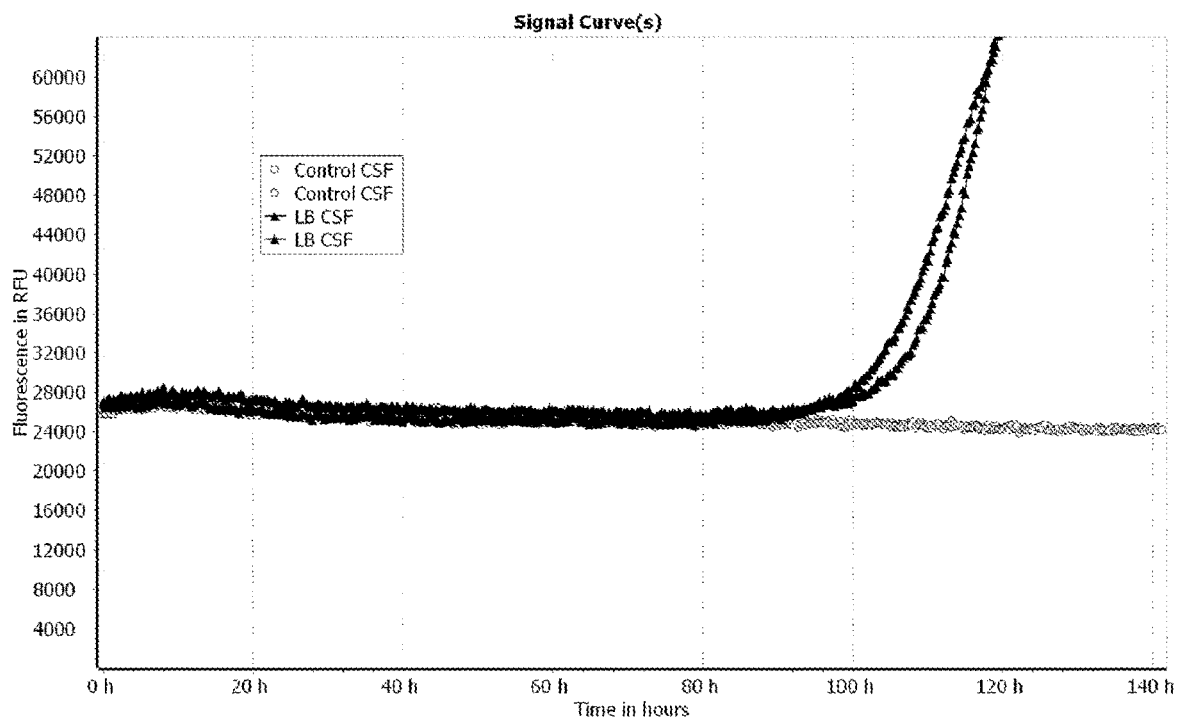
FIG. 16: RT-QuIC traces for CSF samples from patients with Lewy Body disease (LB) or from control subjects with the addition of 37 mg of (A) 0.1 mm zirconium/silica beads, (B) 0.5 mm zirconium/silica beads and (C) 2.3 mm zirconium/silica beads.
Figure 16:
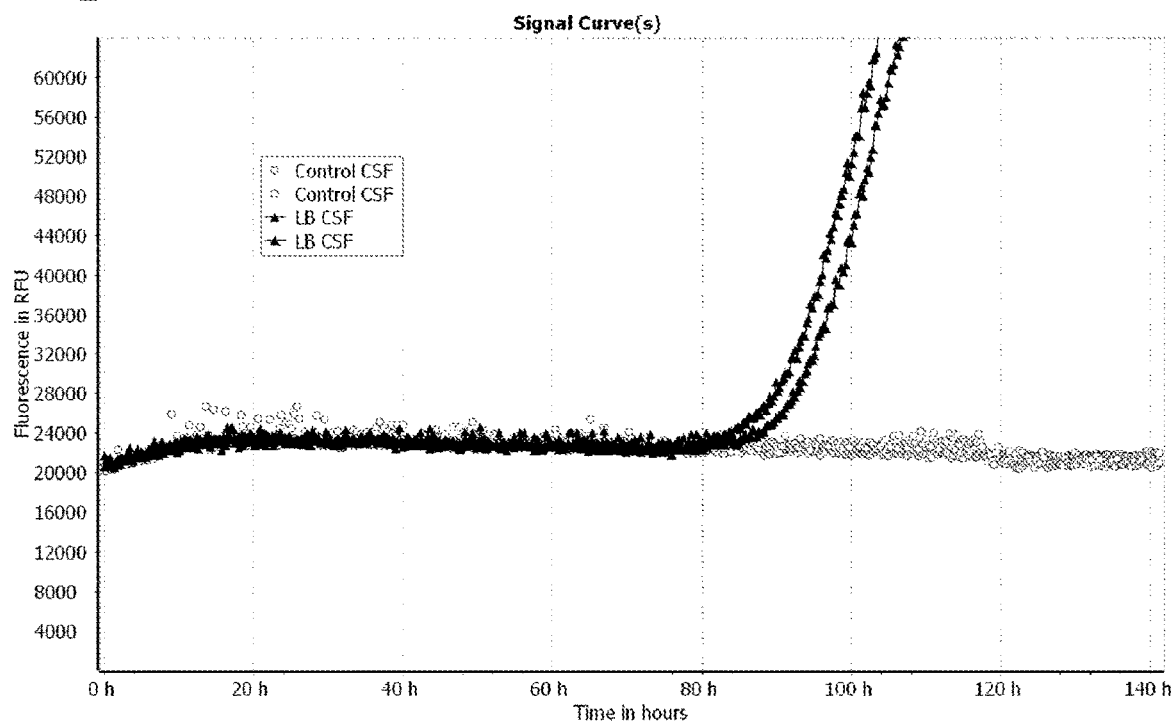
Figure 16:
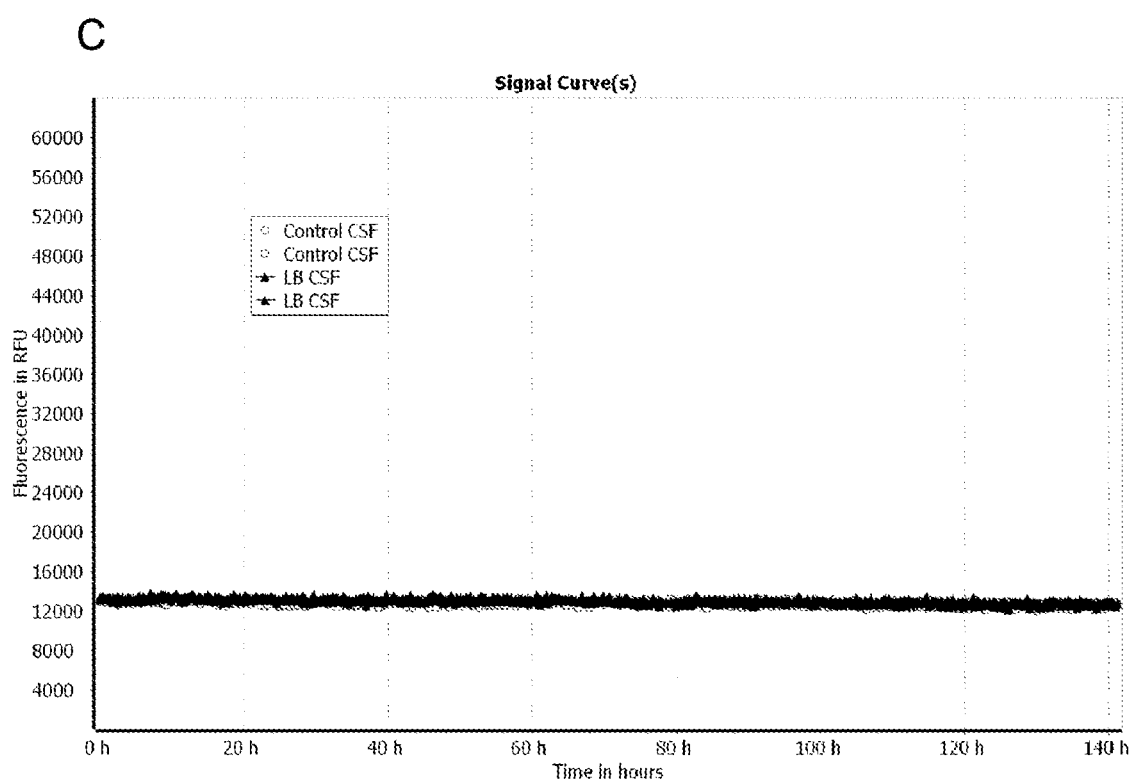

The results from the experiments illustrated in FIGS. 15 and 16 demonstrate that the use of 2.3 mm zirconium/silica does not accelerate the a-syn RT-QuIC reaction seeded by either BH or CSF from LB patients. The results a-syn RT-QuIC reactions using either the 0.1 mm or the 0.5 mm zirconium/silica beads were similar, although a-syn RT-QuIC reactions using the 0.1 mm zirconium/silica beads resulted in ADBH inducing a positive reaction. Handling 0.1 mm zirconium/silica beads was difficult as the very small size meant they were more prone to static than the larger 0.5 mm zirconium/silica. Therefore all further investigations into the composition of the beads were undertaken beads of 0.5 mm in diameter.

Figure 17:
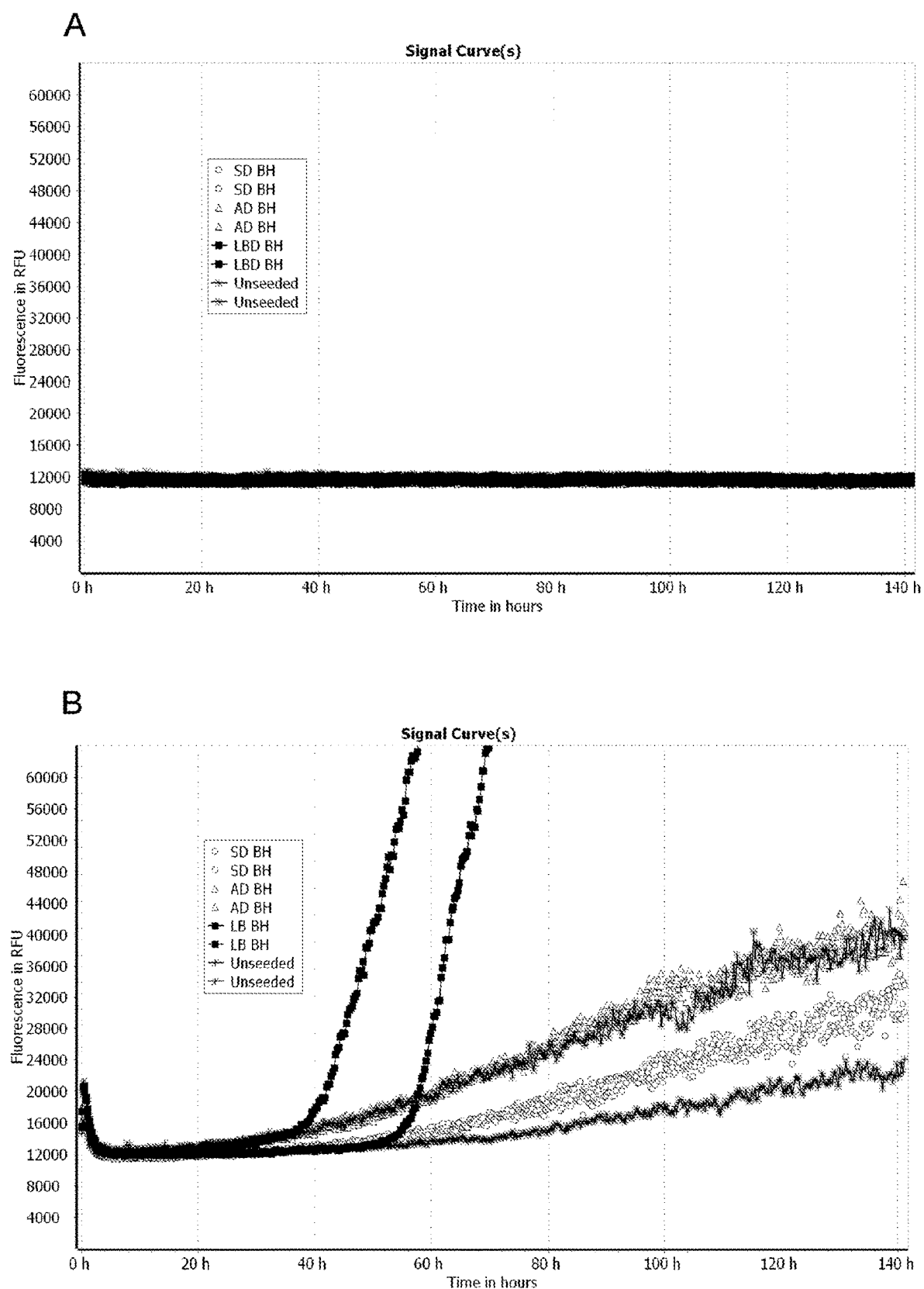
FIG. 17: RT-QuIC traces for BH samples from control subjects (SDBH), Lewy body disease patients (LBDBH) and Alzheimer's Disease (ADBH) and compared to those reactions left unseeded using (A) 0.5 mm steel beads or (B) 0.5 mm glass beads.

3. A-Syn RT-QuIC Reactions Using 0.5 mm Steel and 0.5 mm Glass Beads Seeded with BHs RT-QuIC reactions with the addition of 37 mg of 0.5 mm steel or glass beads were seeded with 5 μL of 1:200,000 dilution of identical BH from control subjects (SDBH), Lewy body disease patients (LBDBH) and Alzheimer's Disease (ADBH) and compared to those reactions left unseeded. The a-syn RT-QuIC reactions using 0.5 m steel beads are shown in FIG. 17A and those for glass beads are shown in FIG. 17B.

The use of 0.5 mm steel beads does not support a-syn RT-QuIC reactions seeded with LBDBH. In contrast the use of 0.5 mm glass beads does result in positive a-syn RT-QuIC reactions seeded with LBDBH, however the unseeded and ADBH seeded reactions show a gradual increase in fluorescence resulting in a lack of a steady baseline.

Figure 18:
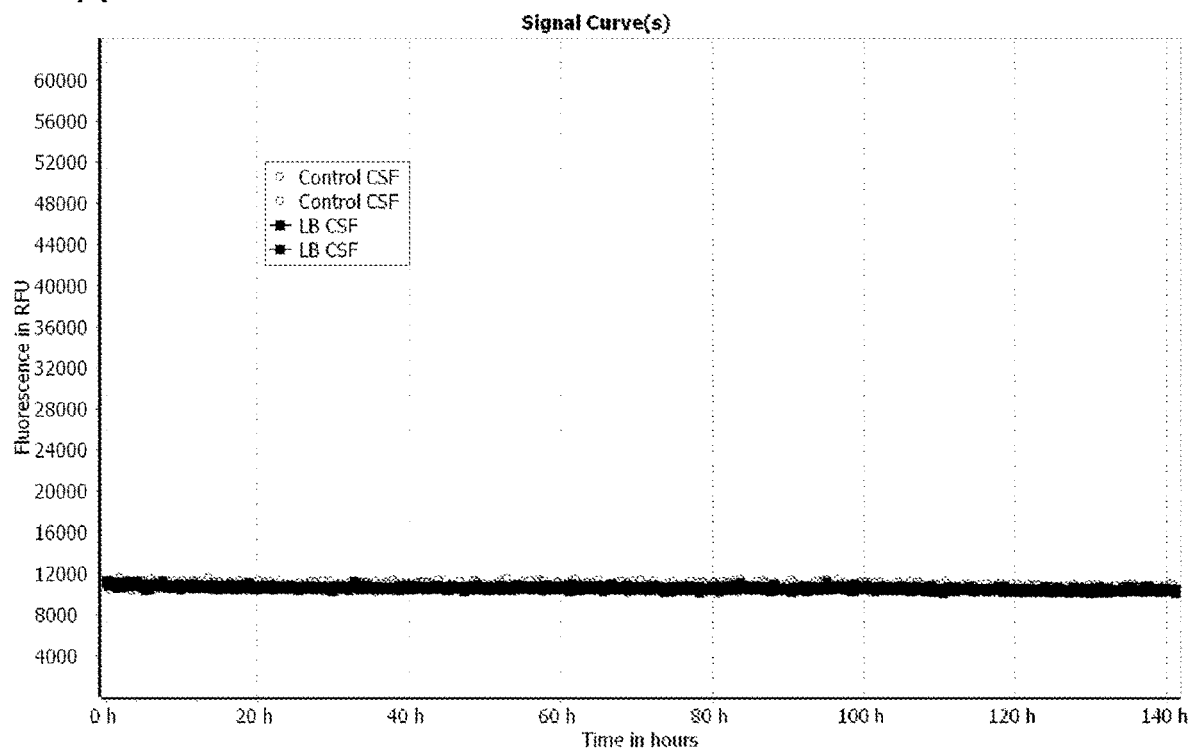
FIG. 18: RT-QuIC traces for CSF samples from control subjects, and Lewy body disease patients (LBDBH) and compared to those reactions left unseeded using (A) 0.5 mm steel beads or (B) 0.5 mm glass beads.
Figure 18:
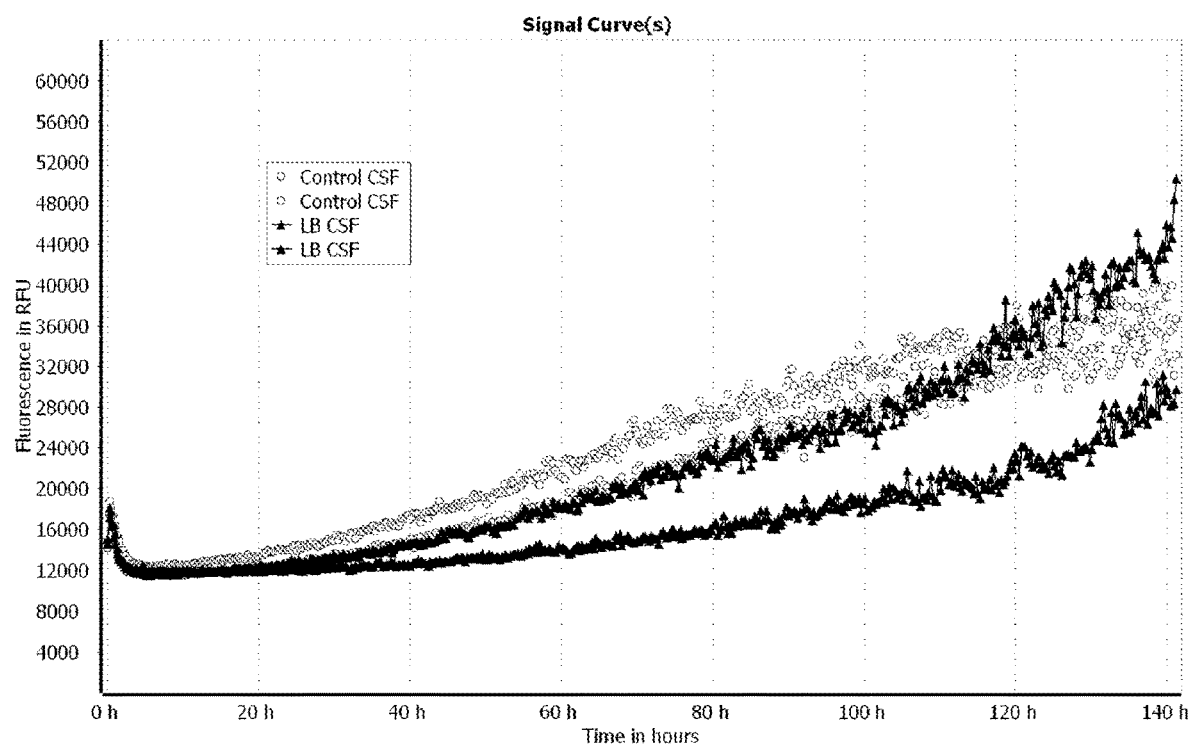

4. A-Syn RT-QuIC Reactions Using 0.5 mm Steel and 0.5 mm Glass Beads Seeded with CSF Samples RT-QuIC reactions with the addition of 37 mg of 0.5 mm steel or glass beads were seeded with 15 μL CSF samples from patients with Lewy Body disease (LB) or from control subjects. The a-syn RT-QuIC reactions seeded with CSF using 0.5 m steel beads are shown in FIG. 18A and those for glass beads are shown in FIG. 18B. The use of steel beads inhibits the ability of CSF samples from LB patients to seed the a-syn RT-QuIC, whilst the use of glass beads results in non-specific increase in fluorescence and also does not support the a-syn RT-QuIC reaction.

The overall conclusion from the above experiments is that the addition of 37 mg/well of 0.5 mm zirconium/silica beads is the best promoter of a-syn RT-QuIC reactions seeded with either BH or CSF samples from patients with LBD.

Investigation of the Ability of Blood Components from Parkinson's Disease (PD) Patients to Seed the Alpha-Synuclein (a-Syn) Real-Time Quaking Induced Conversion (RT-QuIC)

Figure 19:
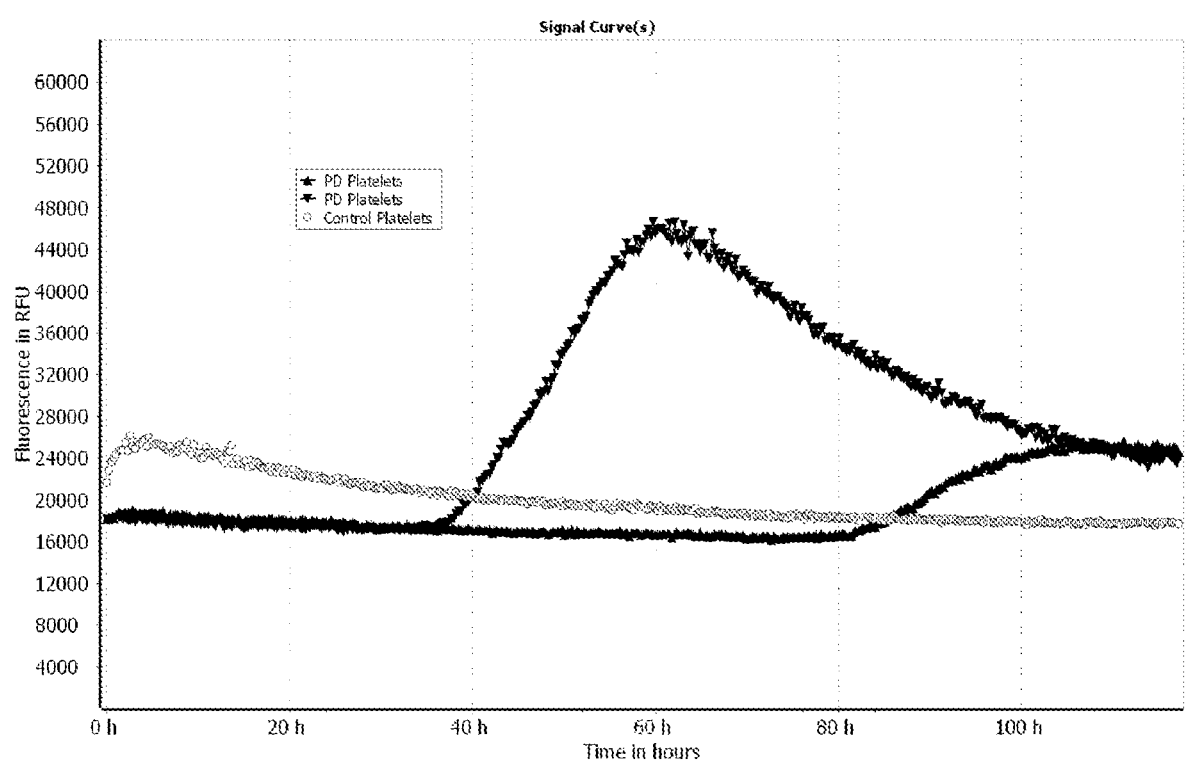
FIG. 19: RT-QuIC traces for platelet samples isolated form EDTA anti-coagulated blood samples from PD and control subjects.

Platelets were isolated from EDTA anti-coagulated blood samples from two PD patients and a control subject. By increasing the shaking speed from 200 rpm to 600 rpm and the temperature of the reaction to 42° C. it was possible to seed the a-syn RT-QuIC reaction using 15 μL of platelets from these 2 patients with PD (FIG. 19). In contrast the platelets from the control subject failed to seed the reaction. Therefore, this demonstrated that the method of the invention is effective at determining whether a blood sample comprises aggregates of a-syn, and therefore to potentially diagnose whether the subject from whom the blood sample originated has an alpha-synucleinopathy such as Parkinson's Disease or Dementia with Lewy Bodies.

REFERENCES

1. Spillantini M G, Divane A, and Goedert M. Assignment of human alpha-synuclein (SNCA) and beta-synuclein (SNCB) geners to chromosome 4q21 and 5q35. Genomics. 1995; 27:379-381.
2. Goedert M, Spillantini M G, Del Tredici K, et al. 100 years of Lewy pathology. Nat Rev Neurol. 2013; 9:13-24.
3. Martf M J, Tolsa E, and Campdelacreu J. Clinical Overview of the Synucleinopathies. Movement disorders. 2003; 18:S21-S27.

4. Mollenhauer M, Cullen V, Kahn I, et al. Direct quantification of CSF alpha-synuclein by ELISA and first cross-sectional study in patients with neurodegeneration. Exp Neurol. 2008; 213:315-325.
5. Williams S M, Schult P, and Sierks MR. Oligomeric a-synuclein an B-amyloid variants as potential biomarkers for Parkinson's and Alzheimer's diseases. Eur J Neurosci. 2015.
6. Shi M, Bradner J, and Hancock AM. Cerebrospinal fluid biomarkers for Parkinson's disease diagnosis and progression. Annals of Neurology. 2011; 69:570-580.
7. Ohrfelt A, Grognet P. Andreasen N. et al. Cerebrospinal fluid alpha-synuclein in neurodegenerative disorders—a marker of synapse loss? Neuroscience Letts. 2009; 450: 332-335.
8. Hong Z, Shi M, Chung K A, et al. DJ-1 and alpha-synucelin in human cerebrospinal fluid as biomarkers of Parkinson's disease. Brain. 2010; 133:713-726.
9. Kruse N, Persson S. Alcolea D. et al. Validation of a quantitative cerebrospinal fluid alpha-synuclein assay in a European-wide interlaboratory study. Neurobiol aging. 2015; 36:2587-2596.
10. Bernis M E, Babila J T, Breid S, et al. Prion-lie propagation of human brain-derived alpha-synuclein in transgenic mice expressing human wild-type alpha-synuclein. Acta Neuropathol Commun. 2015; 3.
11. Brandel J P, Corbille A G, Derkinderen P, et al. Is Parkinson's disease a prion disease? Rev Neurol (Paris). 2015; 171:812-824.
12. L McGuire, A Peden, C Orru, et al. Prion seeding activity in cerebrospinal fluid from patients with sporadic Creutzfeldt-Jakob disease patients using real-time QuIC analysis: a potential new clinical diagnostic test with high sensitivity and specificity. Annals of Neurology 72 (2), 278-285.
13. Clarke R, Smith A D, Jobst K A, et al. Folate, Vitamin B12 and serum total homocysteine levels n confirmed Alzheimer's disease. Archives of Neurology. 1998; 55:1449-1455.
14. Szewwczyk-Krolikowski K, Tomlinson P, Nithi K, et al. The influence of age and gender on motor and non-motor features of early parkinson's disease: initial findings form the Oxford Parkinson Disease Center (OPDC) discovery cohort. Parkinsonism Relat Disord. 2014; 20:99-105.
15. Hughes A J, Daniel S E, Kilford L, et al. Accuracy of clinical diagnosis of idiopathic Parkinson's disease—a clinicopathological study of 100 cases. J Neurol Neurosurg Psychiatry. 1992; 55:181-184.
16. Rolinski M, Zokaei N, Baig F, et al. Visual short-term memory deficits in REM sleep behaviour disordermirror those in parkinson's disease. Brain. 2016; 139:47-53.
17. Iranzo A, Tolosa E, Gelpi E, et al. Neurodegenerative disease status and post-mortem pathology in idiopathic rapid-eye-movement sleep behaviour disorder: an observational cohort study. Lancet. 2013; 12:443-453.
18. Thomas J Montine, Creighton H Phelps, Thomas G Beach, et al. National Institute on Aging-Alzheimer's Association guidleines for the neuropathological assessment of Alzheimer's disease: a practical approach. Acta Neuropathol. 2012; 123:1-11.
19. Kovacs G G, Alafuzoff I, A-SS, Arzberger T, et al. Mixed brain pathologies in dementia:the BrainNet Europe consortium experience. Dement Geriatr Cogn Disord. 2008; 26:343-350.
20. Iranzo A, Tolosa E, Gelpi E, et al. Neurodegenerative disease status and post-mortem pathology in idiopathic rapid-eye-movement sleep behaviour disorder: an observational cohort study. Lancet. 2013; 12:443-453.

The invention claimed is:

1. A method for detecting the presence of alpha-synuclein aggregation in a human cerebrospinal fluid ("CSF") sample, the method comprising the steps:
   (i) providing a human CSF sample;
   (ii) providing a reaction sample comprising:
      (a) a population of beads, wherein the population of beads have a mean diameter of the beads from 1 mm+10% to 0.001 mm+10%, and wherein the population of beads are at least one of: (1) exclusive of magnetic beads; and (2) chemically inert;
      (b) a fluorophore adapted to bind to protein aggregates and to increase fluorescence when bound to protein aggregates; and
      (c) alpha-synuclein or a fragment or variant thereof;
   (iii) combining the human CSF sample and the reaction sample to form a reaction mixture;
   (iv) incubating the reaction mixture with intermittent agitation cycles;
   (v) illuminating the reaction mixture with a wavelength of light that excites the fluorophore; and
   (vi) determining the level of fluorescence of the reaction mixture during incubation,
   wherein a significant increase in the fluorescence of the reaction mixture during steps (iv) to (vi) is indicative of the presence of aggregates of alpha-synuclein in the reaction mixture, and wherein the presence of aggregates of alpha-synuclein in the reaction mixture is indicative of the presence of aggregates of alpha-synuclein in the human CSF sample.

2. The method according to claim 1, wherein the reaction sample is a buffered reaction sample, and wherein the reaction sample is buffered to maintain the pH of the reaction sample from pH 6 to pH 8.5.

3. The method according to claim 1, wherein the fluorophore is a thioflavin or cyanine T-284.

4. The method according to claim 1, wherein the reaction sample comprises from 0.01 mg/mL to 10 mg/mL alpha-synuclein or a fragment or variant thereof to act as an aggregation substrate.

5. The method according to claim 1, wherein the beads of the population of beads of the reaction sample comprise zirconia/silica, glass, or a combination thereof.

6. The method according to claim 1, wherein the population of beads have a mean diameter of the beads from 1 mm+10% to 0.1 mm+10%.

7. The method according to claim 1, wherein the reaction sample comprises from 1 mg to 150 mg of beads per 100 μL of reaction mixture.

8. A method for detecting the presence of alpha-synuclein aggregation in a human blood sample, the method comprising the steps:
   (i) providing a human blood sample;
   (ii) providing a reaction sample comprising:
      (a) a first population of beads, wherein the first population of beads have a mean diameter of the beads from 1 mm+10% to 0.001 mm±10%, and wherein the first population of beads are at least one of: (1) exclusive of magnetic beads; and (2) chemically inert;
      (b) a fluorophore adapted to bind to protein aggregates and to increase fluorescence when bound to protein aggregates; and
      (c) alpha-synuclein or a fragment or variant thereof;
   (iii) combining the human blood sample and the reaction sample to form a reaction mixture;
   (iv) incubating the reaction mixture with intermittent agitation cycles;
   (v) illuminating the sample reaction mixture with a wavelength of light that excites the fluorophore of the reaction sample; and
   (vi) determining the level of fluorescence of the reaction mixture during incubation,
   wherein a significant increase in the fluorescence of the reaction mixture during steps (iv) to (vi) is indicative of the presence of aggregates of alpha-synuclein in the reaction mixture, and wherein the presence of aggregates of alpha-synuclein in the reaction mixture is indicative of the presence of aggregates of alpha-synuclein in the human blood sample.

9. The method according to claim 8, wherein the reaction sample is a buffered reaction sample, and wherein the reaction sample is buffered to maintain the pH of the reaction sample from pH 6 to pH 8.5.

10. The method according to claim 8, wherein the fluorophore is a thioflavin or cyanine T-284.

11. The method according to claim 8, wherein the reaction sample comprises from 0.01 mg/mL to 10 mg/mL alpha-synuclein or a fragment or variant thereof to act as an aggregation substrate.

12. The method according to claim 8, wherein the beads of the population of beads of the reaction sample comprise zirconia/silica, glass, or a combination thereof.

13. The method according to claim 8, wherein the population of beads have a mean diameter of the beads from 1 mm+10% to 0.1 mm+10%.

14. The method of claim 8, further comprising treating the human blood sample prior to step (i) to concentrate any alpha-synuclein present in the human blood sample or to extract alpha-synuclein from the human blood sample.

15. The method of claim 14, wherein the treating the human blood sample comprises treating with a population of beads comprising a magnetic material.

16. A method for diagnosing Parkinson's Disease or Dementia with Lewy bodies in a subject, the method comprising the steps:
   (i) providing a biological sample obtained from the subject;
   (ii) providing a reaction sample comprising:
      (a) a population of beads, wherein the population of beads have a mean diameter of the beads from 1 mm+10% to 0.001 mm+10%, and wherein the first population of beads are at least one of: (1) exclusive of magnetic beads; and (2) chemically inert;
      (b) a fluorophore adapted to bind to protein aggregates and to increase fluorescence when bound to protein aggregates; and
      (c) alpha-synuclein or a fragment or variant thereof;

(iii) combining the biological sample and the reaction sample to form a reaction mixture;
(iv) incubating the reaction mixture with intermittent agitation cycles;
(v) illuminating the reaction mixture with a wavelength of light that excites the fluorophore; and
(vi) determining the level of fluorescence of the reaction mixture during incubation,
wherein a significant increase in the fluorescence of the reaction mixture during steps (iv) to (vi) is indicative of the presence of aggregates of alpha-synuclein in the reaction mixture, wherein the presence of aggregates of alpha-synuclein in the reaction mixture is indicative of the presence of aggregates of alpha-synuclein in the biological sample, and wherein the presence of aggregates of alpha-synuclein in the biological sample is indicative of the subject having Parkinson's Disease or Dementia with Lewy bodies.

\* \* \* \* \*

SEQUENCE LISTING

```
<160> NUMBER OF SEQ ID NOS: 1

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125
```

```
Ser Glu Glu Gly Tyr Gln Asp Tyr Glu Pro Glu Ala
    130                 135                 140
```